United States Patent
Esfandiari

(10) Patent No.: US 10,598,657 B2
(45) Date of Patent: Mar. 24, 2020

(54) IMMUNOASSAY UTILIZING TRAPPING CONJUGATE

(71) Applicant: Chembio Diagnostic Systems, Inc., Medford, NY (US)

(72) Inventor: Javanbakhsh Esfandiari, Stony Brook, NY (US)

(73) Assignee: Chembio Diagnostic Systems, Inc., Medford, NY (US)

(*) Notice: Subject to any disclaimer, the term of this patent is extended or adjusted under 35 U.S.C. 154(b) by 0 days.

(21) Appl. No.: 15/955,595

(22) Filed: Apr. 17, 2018

(65) Prior Publication Data

US 2018/0292401 A1 Oct. 11, 2018

Related U.S. Application Data

(60) Continuation-in-part of application No. 15/878,801, filed on Jan. 24, 2018, now Pat. No. 10,473,655, which is a division of application No. 14/631,084, filed on Feb. 25, 2015, now Pat. No. 9,885,710.

(60) Provisional application No. 61/974,060, filed on Apr. 2, 2014.

(51) Int. Cl.
*G01N 33/543* (2006.01)
*G01N 33/53* (2006.01)
*G01N 33/558* (2006.01)
*G01N 33/569* (2006.01)

(52) U.S. Cl.
CPC ... *G01N 33/54386* (2013.01); *G01N 33/5306* (2013.01); *G01N 33/54366* (2013.01); *G01N 33/558* (2013.01); *G01N 33/56983* (2013.01); *G01N 33/56988* (2013.01); *G01N 2333/11* (2013.01); *G01N 2333/161* (2013.01); *G01N 2469/10* (2013.01); *G01N 2469/20* (2013.01)

(58) Field of Classification Search
CPC ......... G01N 33/54386; G01N 33/5306; G01N 33/558; G01N 33/56983; G01N 33/56988; G01N 33/54366
See application file for complete search history.

(56) References Cited

U.S. PATENT DOCUMENTS

| | | | |
|---|---|---|---|
| 3,960,488 A | 6/1976 | Giaever | |
| 4,041,146 A | 8/1977 | Giaever | |
| 4,042,335 A | 8/1977 | Clement | |
| 4,059,405 A | 11/1977 | Sodickson et al. | |

(Continued)

FOREIGN PATENT DOCUMENTS

| | | |
|---|---|---|
| DE | 19917093 | 10/2000 |
| DE | 10313158 | 10/2004 |

(Continued)

OTHER PUBLICATIONS

"Testing for p24 Antigen," Centers for Disease Control and Prevention. Model Performance Evaluation Program. Human Immunodeficiency Virus Type 1 (HIV-1), 2002.

(Continued)

*Primary Examiner* — Melanie Brown
(74) *Attorney, Agent, or Firm* — Gordon & Jacobson, P.C.

(57) ABSTRACT

Test devices are provided for determining the presence of a first ligand in a sample. In some embodiments depletion conjugates are used to deplete the ligands different from but related to the first ligands from the sample. In some embodiments, interim binding agents are used to enhance the test signal.

27 Claims, 10 Drawing Sheets

(56) References Cited

U.S. PATENT DOCUMENTS

| | | |
|---|---|---|
| 4,094,647 A | 6/1978 | Deutsch et al. |
| 4,144,306 A | 3/1979 | Figueras |
| 4,235,601 A | 11/1980 | Deutsch et al. |
| 4,313,734 A | 2/1982 | Leuvering |
| 4,323,536 A | 4/1982 | Columbus |
| 4,361,537 A | 11/1982 | Deutsch et al. |
| 4,366,241 A | 12/1982 | Tom et al. |
| 4,373,932 A | 2/1983 | Gribnau et al. |
| 4,522,786 A | 6/1985 | Ebersole |
| 4,532,107 A | 7/1985 | Siddigi |
| 4,588,555 A | 5/1986 | Provonchee |
| 4,595,654 A | 6/1986 | Reckel et al. |
| 4,632,901 A | 12/1986 | Valkirs et al. |
| 4,668,619 A | 5/1987 | Greenquist et al. |
| 4,703,017 A | 10/1987 | Campbell et al. |
| 4,740,468 A | 4/1988 | Weng et al. |
| 4,770,853 A | 9/1988 | Bernstein |
| 4,786,595 A | 11/1988 | Arai et al. |
| 4,826,759 A | 5/1989 | Guire et al. |
| 4,855,240 A | 8/1989 | Rosenstein et al. |
| 4,857,453 A | 8/1989 | Ullman et al. |
| 4,870,003 A | 9/1989 | Kortright et al. |
| 4,886,742 A | 12/1989 | Kortright et al. |
| 4,906,439 A | 3/1990 | Grenner |
| 4,912,034 A | 3/1990 | Kalra et al. |
| 4,920,046 A | 4/1990 | McFarland et al. |
| 4,943,522 A | 7/1990 | Eisinger et al. |
| 4,956,275 A | 9/1990 | Zuk et al. |
| 4,956,302 A | 9/1990 | Gordon et al. |
| 4,960,691 A | 10/1990 | Gordon et al. |
| 4,960,710 A | 10/1990 | Lau |
| 4,981,785 A | 1/1991 | Nayak |
| 4,981,786 A | 1/1991 | Dafforn et al. |
| 5,004,584 A | 4/1991 | Rayman |
| 5,006,464 A | 4/1991 | Chu et al. |
| 5,006,474 A | 4/1991 | Horstman et al. |
| 5,075,077 A | 12/1991 | Durley, III et al. |
| 5,075,078 A | 12/1991 | Osikowicz |
| 5,087,556 A | 2/1992 | Ertinghausen |
| 5,091,153 A | 2/1992 | Bachand |
| 5,104,793 A | 4/1992 | Buck |
| 5,104,811 A | 4/1992 | Berger et al. |
| 5,110,550 A | 5/1992 | Schlipfenbacher et al. |
| 5,132,208 A | 7/1992 | Freitag et al. |
| 5,137,808 A | 8/1992 | Ullman et al. |
| 5,147,780 A | 9/1992 | Pouletty et al. |
| 5,156,952 A | 10/1992 | Litman et al. |
| 5,162,238 A | 11/1992 | Eikmeier et al. |
| 5,169,789 A | 12/1992 | Bernstein |
| 5,173,433 A | 12/1992 | Bachand |
| 5,200,321 A | 4/1993 | Kidwell |
| 5,202,268 A | 4/1993 | Kuhn et al. |
| 5,215,446 A | 6/1993 | Takahashi et al. |
| 5,217,905 A | 6/1993 | Marchand et al. |
| 5,219,762 A | 6/1993 | Katamine et al. |
| 5,223,436 A | 6/1993 | Freitag et al. |
| RE34,312 E | 7/1993 | Geiger et al. |
| 5,232,835 A | 8/1993 | Litman et al. |
| 5,238,649 A | 8/1993 | Nason |
| 5,240,735 A | 8/1993 | Lau |
| 5,244,631 A | 9/1993 | Morikawa |
| 5,244,788 A | 9/1993 | Hubscher |
| RE34,405 E | 10/1993 | Gould et al. |
| 5,252,496 A | 10/1993 | Kang et al. |
| 5,275,785 A | 1/1994 | May et al. |
| 5,281,540 A | 1/1994 | Merkh et al. |
| 5,296,192 A | 3/1994 | Carroll et al. |
| 5,300,439 A | 4/1994 | Charlton |
| 5,306,623 A | 4/1994 | Kiser et al. |
| 5,308,775 A | 5/1994 | Donovan et al. |
| 5,332,548 A | 7/1994 | Moore |
| 5,334,502 A | 8/1994 | Sangha |
| 5,338,513 A | 8/1994 | Schlipfenbacher et al. |
| 5,340,748 A | 8/1994 | Baugher et al. |
| 5,356,782 A | 10/1994 | Moorman et al. |
| 5,362,654 A | 11/1994 | Pouletty |
| 5,369,007 A | 11/1994 | Kidwell |
| 5,384,264 A | 1/1995 | Chen et al. |
| 5,391,478 A | 2/1995 | Greene et al. |
| 5,399,316 A | 3/1995 | Yamada |
| 5,411,858 A | 5/1995 | McGeehan et al. |
| 5,418,136 A | 5/1995 | Miller et al. |
| 5,418,142 A | 5/1995 | Kiser et al. |
| 5,418,167 A | 5/1995 | Matner et al. |
| 5,424,215 A | 6/1995 | Albarella et al. |
| 5,424,220 A | 6/1995 | Goerlach-Graw et al. |
| 5,435,970 A | 7/1995 | Mamenta et al. |
| 5,451,504 A | 9/1995 | Fitzpatrick et al. |
| 5,468,648 A | 11/1995 | Chandler |
| 5,470,713 A | 11/1995 | El Shami et al. |
| 5,474,902 A | 12/1995 | Uylen et al. |
| 5,482,830 A | 1/1996 | Bogart et al. |
| 5,494,830 A | 2/1996 | Hubscher |
| 5,500,350 A | 3/1996 | Baker et al. |
| 5,501,985 A | 3/1996 | Baugher et al. |
| 5,514,557 A | 5/1996 | Moghaddam |
| 5,521,102 A | 5/1996 | Boehringer et al. |
| 5,532,133 A | 7/1996 | Barnwell |
| 5,541,057 A | 7/1996 | Bogart et al. |
| 5,550,063 A | 8/1996 | Bogart |
| 5,552,272 A | 9/1996 | Bogart |
| 5,558,834 A | 9/1996 | Chu et al. |
| 5,559,041 A | 9/1996 | Kang et al. |
| 5,567,594 A | 10/1996 | Calenoff |
| 5,571,667 A | 11/1996 | Chu et al. |
| 5,591,645 A | 1/1997 | Rosenstein |
| 5,602,040 A | 2/1997 | May et al. |
| 5,604,110 A | 2/1997 | Baker et al. |
| 5,607,863 A | 3/1997 | Chandler |
| 5,616,467 A | 4/1997 | Olsen et al. |
| 5,620,845 A | 4/1997 | Gould et al. |
| 5,622,871 A | 4/1997 | May et al. |
| 5,624,809 A | 4/1997 | Skold et al. |
| 5,629,164 A | 5/1997 | Rivers |
| 5,629,214 A | 5/1997 | Crosby |
| 5,639,671 A | 6/1997 | Bogart et al. |
| 5,641,639 A | 6/1997 | Perry |
| 5,648,274 A | 7/1997 | Chandler |
| 5,656,503 A | 8/1997 | May et al. |
| 5,658,723 A | 8/1997 | Oberhardt |
| 5,658,801 A | 8/1997 | Poissant et al. |
| 5,670,381 A | 9/1997 | Jou et al. |
| 5,686,315 A | 11/1997 | Pronovost et al. |
| 5,695,928 A | 12/1997 | Stewart |
| 5,695,930 A | 12/1997 | Weinstein et al. |
| 5,710,005 A | 1/1998 | Rittenburg |
| 5,714,341 A | 2/1998 | Thieme et al. |
| 5,714,389 A | 2/1998 | Charlton et al. |
| 5,723,345 A | 3/1998 | Yamauchi et al. |
| 5,726,010 A | 3/1998 | Clark |
| 5,728,587 A | 3/1998 | Kang et al. |
| 5,736,188 A | 4/1998 | Alcock et al. |
| 5,739,041 A | 4/1998 | Nazareth et al. |
| 5,743,960 A | 4/1998 | Tisone |
| 5,750,333 A | 5/1998 | Clark |
| 5,766,961 A | 6/1998 | Pawlak et al. |
| 5,766,962 A | 6/1998 | Childs et al. |
| 5,770,460 A | 6/1998 | Pawlak et al. |
| 5,773,234 A | 6/1998 | Pronovost et al. |
| 5,786,220 A | 7/1998 | Pronovost et al. |
| 5,798,273 A | 8/1998 | Schuler et al. |
| 5,804,391 A | 9/1998 | Klemt et al. |
| 5,807,756 A | 9/1998 | Bauman et al. |
| 5,814,522 A | 9/1998 | Zimmer et al. |
| 5,824,268 A | 10/1998 | Bernstein et al. |
| 5,827,646 A | 10/1998 | Middeldorp et al. |
| 5,846,838 A | 12/1998 | Chandler |
| 5,853,670 A | 12/1998 | Bunce |
| 5,861,265 A | 1/1999 | Perry |
| 5,869,272 A | 2/1999 | Bogart et al. |
| 5,869,345 A | 2/1999 | Chandler |
| 5,872,713 A | 2/1999 | Douglas et al. |
| 5,874,216 A | 2/1999 | Mapes |
| 5,877,028 A | 3/1999 | Chandler et al. |

(56) References Cited

U.S. PATENT DOCUMENTS

| | | |
|---|---|---|
| 5,879,951 A | 3/1999 | Sy |
| 5,885,526 A | 3/1999 | Chu |
| 5,885,527 A | 3/1999 | Buechler |
| 5,891,650 A | 4/1999 | Godowski et al. |
| 5,900,379 A | 5/1999 | Noda et al. |
| 5,902,722 A | 5/1999 | Di Cesare et al. |
| 5,912,116 A | 6/1999 | Caldwell |
| 5,922,533 A | 7/1999 | Vallari et al. |
| 5,922,615 A | 7/1999 | Nowakowski et al. |
| 5,935,331 A | 8/1999 | Naka et al. |
| 5,939,252 A | 8/1999 | Lennon et al. |
| 5,939,272 A | 8/1999 | Buechler et al. |
| 5,948,695 A | 9/1999 | Douglas et al. |
| 5,955,377 A | 9/1999 | Maul et al. |
| 5,958,790 A | 9/1999 | Cerny |
| 5,965,458 A | 10/1999 | Kouvonen et al. |
| 5,972,720 A | 10/1999 | Nichtl et al. |
| 5,976,895 A | 11/1999 | Cipkowski |
| 5,985,675 A | 11/1999 | Charm et al. |
| 5,989,921 A | 11/1999 | Charlton et al. |
| 5,998,220 A | 12/1999 | Chandler |
| 5,998,221 A | 12/1999 | Malick et al. |
| 6,008,056 A | 12/1999 | Thieme |
| 6,017,767 A | 1/2000 | Chandler |
| 6,027,890 A | 2/2000 | Ness et al. |
| 6,040,195 A | 3/2000 | Carroll et al. |
| 6,046,013 A | 4/2000 | Tidey et al. |
| 6,046,057 A | 4/2000 | Nazareth et al. |
| 6,057,166 A | 5/2000 | Childs et al. |
| 6,060,326 A | 5/2000 | Frank et al. |
| 6,063,337 A | 5/2000 | Markart |
| 6,087,184 A | 7/2000 | Magginetti et al. |
| 6,106,732 A | 8/2000 | Johnston et al. |
| 6,140,134 A | 10/2000 | Rittenburg |
| 6,140,136 A | 10/2000 | Lee |
| 6,168,956 B1 | 1/2001 | Chandler |
| 6,187,268 B1 | 2/2001 | Albarella et al. |
| 6,187,598 B1 | 2/2001 | May et al. |
| 6,194,220 B1 | 2/2001 | Malick et al. |
| 6,197,494 B1 | 3/2001 | Oberhardt |
| 6,221,625 B1 | 4/2001 | Ashihara et al. |
| 6,221,678 B1 | 4/2001 | Chandler |
| 6,224,831 B1 | 5/2001 | Stafford et al. |
| 6,228,660 B1 | 5/2001 | May et al. |
| 6,235,464 B1 | 5/2001 | Henderson et al. |
| 6,248,598 B1 | 6/2001 | Bogema |
| 6,258,548 B1 | 7/2001 | Buck |
| 6,271,040 B1 | 8/2001 | Buechler |
| 6,271,045 B1 | 8/2001 | Douglas et al. |
| 6,271,046 B1 | 8/2001 | Chandler |
| 6,277,650 B1 | 8/2001 | Nazareth et al. |
| 6,284,550 B1 | 9/2001 | Carroll et al. |
| 6,287,875 B1 | 9/2001 | Geisberg |
| 6,297,020 B1 | 10/2001 | Brock |
| 6,297,060 B1 | 10/2001 | Nowakowski et al. |
| 6,300,142 B1 | 10/2001 | Andrewes et al. |
| RE37,437 E | 11/2001 | Friesen et al. |
| 6,316,205 B1 | 11/2001 | Guan et al. |
| 6,316,264 B1 | 11/2001 | Corey et al. |
| 6,319,676 B1 | 11/2001 | Nazareth et al. |
| 6,326,214 B1 | 12/2001 | Liu et al. |
| 6,335,205 B1 | 1/2002 | Bausback |
| 6,352,862 B1 | 3/2002 | Davis et al. |
| 6,362,008 B1 | 3/2002 | Kohn et al. |
| 6,368,875 B1 | 4/2002 | Geisberg |
| 6,368,876 B1 | 4/2002 | Huang et al. |
| 6,372,514 B1 | 4/2002 | Lee |
| 6,372,515 B1 | 4/2002 | Casterlin et al. |
| 6,372,516 B1 | 4/2002 | Sun |
| 6,376,195 B1 | 4/2002 | Mapes |
| 6,399,398 B1 | 6/2002 | Cunningham et al. |
| 6,403,383 B1 | 6/2002 | Casterlin et al. |
| 6,403,384 B1 | 6/2002 | Lea |
| 6,406,922 B2 | 6/2002 | Casterlin et al. |
| 6,413,473 B1 | 7/2002 | Bacon |
| 6,413,784 B1 | 7/2002 | Lundsgaard et al. |
| 6,436,722 B1 | 8/2002 | Clark et al. |
| 6,455,324 B1 | 9/2002 | Douglas |
| 6,472,226 B1 | 10/2002 | Barradine et al. |
| 6,475,805 B1 | 11/2002 | Charm et al. |
| 6,485,982 B1 | 11/2002 | Charlton |
| 6,489,129 B1 | 12/2002 | Faatz et al. |
| 6,492,127 B2 | 12/2002 | Goodell et al. |
| 6,500,629 B1 | 12/2002 | Cleaver et al. |
| 6,502,766 B1 | 1/2003 | Streutker et al. |
| 6,503,702 B1 | 1/2003 | Stewart |
| 6,503,722 B1 | 1/2003 | Valkirs |
| 6,511,814 B1 | 1/2003 | Carpenter |
| 6,514,769 B2 | 2/2003 | Lee |
| 6,514,773 B1 | 2/2003 | Klein et al. |
| 6,528,321 B1 | 3/2003 | Fitzgerald et al. |
| 6,528,322 B1 | 3/2003 | Carlsson et al. |
| 6,528,323 B1 | 3/2003 | Thayer et al. |
| 6,528,325 B1 | 3/2003 | Hubscher et al. |
| 6,534,324 B1 | 3/2003 | Zin |
| 6,544,474 B2 | 4/2003 | Douglas |
| 6,548,309 B1 | 4/2003 | Moore et al. |
| 6,551,842 B1 | 4/2003 | Carpenter |
| 6,592,815 B1 | 7/2003 | Zimmer |
| 6,593,085 B1 | 7/2003 | Barnett et al. |
| 6,602,719 B1 | 8/2003 | Carpenter |
| 6,617,116 B2 | 9/2003 | Guan et al. |
| 6,623,955 B2 | 9/2003 | Matner et al. |
| 6,627,459 B1 | 9/2003 | Tung et al. |
| 6,632,681 B1 | 10/2003 | Chu |
| 6,645,732 B2 | 11/2003 | Faatz et al. |
| 6,649,418 B1 | 11/2003 | Geisberg |
| 6,656,744 B2 | 12/2003 | Pronovost et al. |
| 6,656,745 B1 | 12/2003 | Cole |
| 6,660,469 B1 | 12/2003 | Wright et al. |
| 6,663,833 B1 | 12/2003 | Stave et al. |
| 6,673,628 B2 | 1/2004 | Freitag et al. |
| RE38,430 E | 2/2004 | Rosenstein |
| 6,686,167 B2 | 2/2004 | Bagaria |
| 6,699,722 B2 | 3/2004 | Bauer et al. |
| 6,703,196 B1 | 3/2004 | Klepp et al. |
| 6,706,539 B2 | 3/2004 | Nelson et al. |
| 6,713,309 B1 | 3/2004 | Anderson et al. |
| 6,727,073 B1 | 4/2004 | Moore et al. |
| 6,737,277 B1 | 5/2004 | Kang et al. |
| 6,750,031 B1 | 6/2004 | Ligler et al. |
| 6,753,190 B1 | 6/2004 | Okada et al. |
| 6,767,710 B2 | 7/2004 | DiNello et al. |
| 6,767,714 B2 | 7/2004 | Nazareth et al. |
| 6,780,651 B2 | 8/2004 | Douglas et al. |
| 6,790,611 B2 | 9/2004 | Lassen et al. |
| 6,797,481 B1 | 9/2004 | Ullman et al. |
| 6,808,889 B2 | 10/2004 | Fitzpatrick et al. |
| 6,808,937 B2 | 10/2004 | Ligler et al. |
| 6,812,038 B1 | 11/2004 | Mendel-Hartvig et al. |
| 6,818,180 B2 | 11/2004 | Douglas et al. |
| 6,818,455 B2 | 11/2004 | May et al. |
| 6,824,975 B2 | 11/2004 | Hubscher et al. |
| 6,824,997 B1 | 11/2004 | Moore et al. |
| 6,828,110 B2 | 12/2004 | Lee et al. |
| RE38,688 E | 1/2005 | Friesen et al. |
| 6,844,200 B2 | 1/2005 | Brock |
| 6,846,635 B1 | 1/2005 | Anderson et al. |
| 6,849,414 B2 | 2/2005 | Guan et al. |
| 6,855,561 B2 | 2/2005 | Jerome et al. |
| 6,863,866 B2 | 3/2005 | Kelly et al. |
| 6,867,051 B1 | 3/2005 | Anderson et al. |
| 6,887,701 B2 | 5/2005 | Anderson et al. |
| 6,905,835 B2 | 6/2005 | Sorell Gomez et al. |
| 6,924,153 B1 | 8/2005 | Boehringer et al. |
| 6,927,068 B2 | 8/2005 | Simonson et al. |
| 6,991,940 B2 | 1/2006 | Carroll et al. |
| 7,018,847 B2 | 3/2006 | Mendel-Hartvig et al. |
| 7,045,342 B2 | 5/2006 | Nazareth et al. |
| 7,049,130 B2 | 5/2006 | Carroll et al. |
| 7,109,042 B2 | 9/2006 | May et al. |
| 7,189,522 B2 | 3/2007 | Esfandiari |
| 7,270,995 B2 | 9/2007 | Matsushita et al. |
| 7,682,801 B2 | 3/2010 | Esfandiari |

(56) References Cited

U.S. PATENT DOCUMENTS

| | | |
|---|---|---|
| 7,879,597 B2 | 2/2011 | Esfandiari |
| 8,507,259 B2 | 8/2013 | Esfandiari |
| 8,603,835 B2 | 12/2013 | Esfandiari |
| 9,885,710 B2 | 2/2018 | Esfandiari |
| 9,891,216 B2 | 2/2018 | Esfandiari |
| 2001/0012637 A1 | 8/2001 | Casterlin et al. |
| 2001/0026942 A1 | 10/2001 | Carpenter et al. |
| 2001/0026944 A1 | 10/2001 | Chung et al. |
| 2001/0034068 A1 | 10/2001 | Spivey et al. |
| 2001/0039057 A1 | 11/2001 | Douglas et al. |
| 2001/0048893 A1 | 12/2001 | Norris et al. |
| 2002/0001853 A1 | 1/2002 | Obremski et al. |
| 2002/0015663 A1 | 2/2002 | Goldstein et al. |
| 2002/0019062 A1 | 2/2002 | Lea et al. |
| 2002/0031839 A1 | 3/2002 | McNeirney et al. |
| 2002/0046614 A1 | 4/2002 | Alley |
| 2002/0048819 A1 | 4/2002 | Alley |
| 2002/0052050 A1 | 5/2002 | Douglas et al. |
| 2002/0057991 A1 | 5/2002 | Kelly et al. |
| 2002/0058330 A1 | 5/2002 | Carroll et al. |
| 2002/0110803 A1 | 8/2002 | Dhar et al. |
| 2002/0119497 A1 | 8/2002 | Wild et al. |
| 2002/0142291 A1 | 10/2002 | Bauer et al. |
| 2002/0155028 A1 | 10/2002 | Wong |
| 2002/0164670 A1 | 11/2002 | Forrest |
| 2002/0172937 A1 | 11/2002 | Dave et al. |
| 2002/0173050 A1 | 11/2002 | Dinello et al. |
| 2002/0192839 A1 | 12/2002 | Mink et al. |
| 2003/0045001 A1 | 3/2003 | Burgess et al. |
| 2003/0049658 A1 | 3/2003 | Smart et al. |
| 2003/0118480 A1 | 6/2003 | Kaylor et al. |
| 2003/0124740 A1 | 7/2003 | Bachand |
| 2003/0138351 A1 | 7/2003 | Etes |
| 2003/0143639 A1 | 7/2003 | Matsushita et al. |
| 2003/0180967 A1 | 9/2003 | Shigetoh |
| 2004/0001767 A1 | 1/2004 | Peters et al. |
| 2004/0014157 A1 | 1/2004 | Sommer et al. |
| 2004/0087036 A1 | 5/2004 | Chung et al. |
| 2004/0142495 A1 | 7/2004 | Hartman et al. |
| 2004/0161859 A1 | 8/2004 | Guo et al. |
| 2004/0184954 A1 | 9/2004 | Guo et al. |
| 2004/0197769 A1 | 10/2004 | Wong et al. |
| 2004/0219694 A1 | 11/2004 | Chittock et al. |
| 2004/0235189 A1 | 11/2004 | Lu |
| 2004/0241779 A1 | 12/2004 | Piasio et al. |
| 2004/0248322 A1 | 12/2004 | Charlton |
| 2005/0074900 A1 | 4/2005 | Morgan et al. |
| 2005/0079629 A1 | 4/2005 | Guo et al. |
| 2005/0112779 A1 | 5/2005 | Wei et al. |
| 2005/0112780 A1 | 5/2005 | Song |
| 2005/0112782 A1 | 5/2005 | Buechler |
| 2005/0130293 A1 | 6/2005 | Blatt et al. |
| 2005/0130319 A1 | 6/2005 | Biegelsen et al. |
| 2005/0136500 A1 | 6/2005 | Yang et al. |
| 2005/0142032 A1 | 6/2005 | Hoenes et al. |
| 2005/0164404 A1 | 7/2005 | Marlborough et al. |
| 2005/0170527 A1 | 8/2005 | Boehringer et al. |
| 2005/0208677 A1 | 9/2005 | Owens et al. |
| 2005/0227371 A1 | 10/2005 | Gokhan |
| 2005/0244985 A1 | 11/2005 | Freitag et al. |
| 2005/0244986 A1 | 11/2005 | May et al. |
| 2006/0099719 A1 | 5/2006 | Curcio |
| 2006/0121626 A1 | 6/2006 | Imrich |
| 2006/0134803 A1 | 6/2006 | Esfandiari |
| 2006/0148097 A1 | 7/2006 | Yamaguchi et al. |
| 2006/0166374 A1 | 7/2006 | Hubscher |
| 2006/0205059 A1* | 9/2006 | Esfandiari ............ G01N 33/538 435/287.2 |
| 2007/0020768 A1 | 1/2007 | Rundstrom et al. |
| 2007/0059682 A1 | 3/2007 | Aberl et al. |
| 2007/0184492 A1 | 8/2007 | Wang et al. |
| 2007/0243630 A1 | 10/2007 | Boehringer et al. |
| 2008/0138842 A1 | 6/2008 | Boehringer et al. |
| 2008/0194013 A1 | 8/2008 | Shida et al. |
| 2008/0318341 A1 | 12/2008 | Esfandiari |
| 2009/0148933 A1 | 6/2009 | Battrell et al. |
| 2009/0181470 A1 | 7/2009 | Chiku et al. |
| 2010/0047857 A1 | 2/2010 | Fong |
| 2010/0112725 A1 | 5/2010 | Babu et al. |
| 2010/0285490 A1 | 11/2010 | Dees et al. |
| 2011/0124130 A1 | 5/2011 | Wagner et al. |
| 2011/0151584 A1 | 6/2011 | Esfandiari |
| 2012/0003727 A1 | 1/2012 | Esfandiari |
| 2012/0282154 A1 | 11/2012 | Slowey et al. |
| 2013/0225448 A1 | 8/2013 | O'Farrell et al. |
| 2013/0309656 A1 | 11/2013 | Davis |
| 2014/0045172 A1 | 2/2014 | Esfandiari |
| 2018/0045722 A1 | 2/2018 | Esfandiari |
| 2018/0149645 A1 | 5/2018 | Esfandiari |
| 2018/0292401 A1 | 10/2018 | Esfandiari |

FOREIGN PATENT DOCUMENTS

| | | |
|---|---|---|
| EP | 0299359 | 1/1989 |
| EP | 1284422 | 2/2003 |
| EP | 2065706 | 6/2009 |
| JP | 05104052 | 4/1993 |
| WO | WO88/08534 | 11/1988 |
| WO | WO1993/03175 | 2/1993 |
| WO | WO1994/06013 | 3/1994 |
| WO | WO03/041733 A1 | 5/2003 |
| WO | WO2004/084274 | 9/2004 |
| WO | WO2005/070324 | 8/2005 |
| WO | WO2009/075894 | 6/2009 |
| WO | WO 2013/105090 | 7/2013 |

OTHER PUBLICATIONS

A printout from http://en.wikipedia.org/wiki/P24retreived on Oct 2, 2012.

"An integrated microfluidic biochemical detection system for protein analysis with magnetic bead-based sampling capabilities," Choi et al., Lab Chip, 2002, 2, pp. 27-30.

Ho, David W. T., et al, Rapid Diagnosis of Acute Epstein-Barr Virus Infection by an Indirect Enzyme-Linked Immunosorbent Assay for Specific Immunoglobulin M (IgM) Antibody without Rheumatoid Factor and Specific IgG Interference; Journal of Clinical Microbiology, vol. 27, No. 5; May 1989, pp. 952-958, American Society for Microbiology.

Martins, Thomas B., et al., An Evaluation of the Effectiveness of Three Immunoglobulin G (IgG) Removal Procedures for Routine IgM Serological Testing; Clinical and Diagnostic Laboratory Immunology, Jan. 1995, vol. 2, No. 1; pp. 98-103; American Society for Microbiology.

Extended European Search Report dated Nov. 8, 2019 of Application No. 19183841.6.

Office Action dated Oct. 29, 2019 of Brazilian Patent Application No. BR112016022829-4.

Written Opinion dated Nov. 4, 2019 of Singapore Patent Application No. 11201608278W.

Australian Office Action dated Jun. 17, 2019 of Application No. 2015241521.

Malaysia Office Action and Search Report dated Dec. 12, 2019 of Application No. PI2016703612.

* cited by examiner

Gold conjugate anti-human IgM

IMMUNOASSAY UTILIZING TRAPPING CONJUGATE

CROSS-REFERENCE TO RELATED APPLICATION

This application is a continuation-in-part of U.S. patent application Ser. No. 15/878,801 filed Jan. 24, 2018 and issued as U.S. Pat. No. 10,473,655, which is a divisional of U.S. patent application Ser. No. 14/631,084, filed Feb. 25, 2015 and issued as U.S. Pat. No. 9,885,710, which claims benefit of U.S. Provisional Application Ser. No. 61/974,060, filed Apr. 2, 2014, all of which are hereby incorporated herein by reference.

BACKGROUND

1. Related Patents

This application relates to co-owned U.S. Pat. Nos. 7,189,522, 7,682,801, 7,879,597, 8,507,259, and 8,603,835, all of which are hereby incorporated by reference herein in their entireties.

2. Field

The subject disclosure relates broadly to immunoassay methods and devices. More particularly, the subject disclosure relates to the detection of one or more particular ligands in a body fluid possibly containing additional related ligands.

3. State of the Art

Many types of ligand-receptor assays have been used to detect the presence of various substances, often generally called ligands, in body fluids such as blood, urine, or saliva. These assays involve antigen antibody reactions, synthetic conjugates comprising radioactive, enzymatic, fluorescent, or visually observable polystyrene or metal sol tags, and specially designed reactor chambers. In all these assays, there is a receptor, e.g., an antibody, which is specific for the selected ligand or antigen, and a means for detecting the presence, and in some cases the amount, of the ligand-receptor reaction product. Some tests are designed to make a quantitative determination, but in many circumstances all that is required is a positive/negative qualitative indication. Examples of such qualitative assays include blood typing, most types of urinalysis, pregnancy tests, and AIDS tests. For these tests, a visually observable indicator such as the presence of agglutination or a color change is preferred.

Co-owned U.S. Pat. Nos. 7,189,522, 7,682,801, 7,879,597, and 8,507,259 are directed to improved rapid detection assays utilizing a "dual path" lateral flow device. More particularly, the immunoassay device is provided with a first sorbent strip that provides a first lateral or horizontal flow path for a conjugate, and a second sorbent strip that provides a second lateral or horizontal flow path for a sample. A test site having an immobilized ligand-binding mechanism is located on or in at least one of the strips, and the strips touch each other at the test site. In use, the sample and a buffer solution are first provided to the second sorbent strip and flow over time to the test site along the second flow path (i.e., they do not immediately wet the test site). If the sample contains ligand of interest, the ligand is captured at the test site by the immobilized ligand-binding mechanism. Buffer solution provided to the first sorbent strip carries the conjugate to the test site after the sample has reached the test site. If ligand is captured at the test site, the conjugate binds to the captured ligand and provides an indication of a "positive" test result; i.e., ligand of interest was present in the sample. If ligand is not captured at the test site, the conjugate does not bind, and a "negative" test results is obtained; i.e., ligand of interest was not present in the sample. A control line that captures conjugate may be provided near the test site to confirm that the test was properly conducted. By providing separate flow paths for the sample and the conjugate, substantially higher sensitivity and selectivity are obtained relative to standard lateral flow devices and reverse-flow devices utilizing single strips.

The dual path devices have also proved to be robust in providing accurate sensitive results where the test site is provided with multiple different immobilized ligand-binding mechanisms; i.e., multiplex capabilities. For example, separate test lines in a single DPP device have been provided for separately and accurately detecting HIV-1, HIV-2, and syphilis.

SUMMARY

In one embodiment a dual path immunoassay test cell device for detecting the presence of a first ligand in a sample is provided with a first sorbent material defining a first horizontal or lateral flow path and a second sorbent material defining a second horizontal or lateral flow path, the first and second sorbent materials overlying one another at a test site. The first flow path has a first location for receiving a first solution, which, in the case of a liquid conjugate system is a conjugate solution, and which, in the case of a dry conjugate system is a buffer solution. Where a buffer solution is utilized, the first sorbent material is provided with a first (mobile) conjugate located downstream of the first location. The second flow path has a second location for receiving a second solution comprising a sample. In one embodiment, the sample is a blood, urine, saliva, or other sample that may be mixed with buffer solution if desired, and immobilized second-ligand binding molecules are located downstream of the second location. The second-ligand binding molecules are related to the first ligand for which the sample is being tested but are not the same. The second sorbent material is distinct or separate from the first sorbent material. The test site is provided with first-ligand binding molecules such as immobilized antigens or antibodies or other molecules such as aptamers, nucleic acids, etc. located where the first and second sorbent materials overlie one another. The first-ligand binding molecules at the test site may be arranged in one or more lines or other distinctive patterns. A control line or site may be provided downstream from the test site.

In one embodiment, the second-ligand binding molecules are second conjugates that include immobilized ligand binding molecules conjugated with particles. In one embodiment, the second conjugate include antigens conjugated with particles. In one embodiment, the particles conjugated with the antigens comprise white latex. In another embodiment, the second conguate includes antibodies conjugated with particles. In one embodiment, the particles conjugate with the antibodies comprise white latex. In one embodiment directed to detecting influenza ("flu"), the second-ligand binding molecules include antigens of at least one influenza ("flu") antigen and the test site is provided with immobilized antigen of at least one influenza antigen different but related to the at least one flu antigen of the immobilized conjugate. In one embodiment, the first conjugate is a gold sol conjugated to protein A.

In another embodiment a dual path immunoassay test cell device for detecting the presence of a first ligand in a sample is provided with a first sorbent material defining a first horizontal flow path and a second sorbent material distinct from the first sorbent material and defining a second horizontal flow path, the first and second sorbent materials overlying one another at a test site. The first flow path has a first location for receiving a first solution, which, in the case of a liquid conjugate system is a conjugate solution, and which, in the case of a dry conjugate system is a buffer solution. Where a buffer solution is utilized, the first sorbent material is provided with a first (mobile) conjugate located downstream of the first location. The second flow path has a second location for receiving a second solution comprising a sample such as blood, urine, saliva, or other sample that has been previously mixed with second-ligand binding molecules and, if desired, buffer and optionally filtered prior to being applied as the second solution to the second location. Where the sample has been mixed with second-ligand binding molecules and not filtered, in one embodiment, the second flow path may include a filter for the second solution. The second-ligand binding molecules are related to the first ligand for which the sample is being tested but are not the same and in one embodiment may include immobilized ligand binding molecules such as antigens or antibodies conjugated with particles such as latex. In one embodiment directed to detecting influenza ("flu"), the second ligand binding molecules include antigens of at least one influenza ("flu") antigen and the test site is provided with immobilized antigen of at least one influenza antigen different but related to the at least one flu antigen of the immobilized conjugate. In one embodiment the test site is provided with first-ligand binding molecules such as immobilized antigens or antibodies or other molecules such as aptamers, nucleic acids, etc. located where the first and second sorbent materials overlie one another. The first-ligand binding molecules at the test site may be arranged in one or more lines or other distinctive patterns. A control line or site may be provided downstream from the test site.

In one aspect, the second-ligand binding molecules are used as a depleting mechanism that captures and thereby depletes antibodies (or antigens) related to the antibodies (or antigens) that are being detected at the test site. By way of example, where the test site includes a pendemic flu-A antigen for identifying the presence of a flu-A antibody in the sample, the second conjugate may be provided with one or more common flu-A antigens and or flu-B antigens. In this manner, common flu-A and flu-B antibodies in the sample that may otherwise be captured or retained at the test site (because of their structure which can be similar in many ways to the related pandemic flu-A antibodies) are generally captured by the second immobilized conjugate; i.e., the number of common flu-A and flu-B antibodies reaching the test site is depleted. As a result, the sensitivity of the test is increased.

In one aspect, the use of a white latex conjugate as the immobilized depleting conjugate reduces the visibility of the conjugate should it be loosened and travel with the sample to the test site and arrive at the test site.

Where the test cell is provided in a housing, the housing is provided with a first opening adjacent the first location and a second opening adjacent the second location. A viewing window is provided in the housing above the test line. Similarly, a viewing window may be provided in the housing above the control line.

According to one set of embodiments, the sorbent materials are laid out in a T shape, where the first location for receiving the buffer or buffer-conjugate solution is located near one end of the top bar of the T, the second location for receiving the sample is located near the end of the stem of the T, and the sorbent materials overlie each other at the intersection. Of course, the sorbent materials may be laid out in other configurations, and the housing may take other shapes, such as rectangular, square, irregular, etc. regardless of the manner in which the sorbent materials are arranged.

In one embodiment of the invention, the materials, thicknesses and lengths of the first and second sorbent materials are chosen to adjust the timing regarding the liquid sample and liquid buffer reaching the test site.

In the dry conjugate system, a first dry conjugate is provided between the first opening and the test site. The first conjugate is supported on or within the sorbent material such that when a buffer is added in the first opening, the sorbent material wicks the buffer to the first conjugate which is then carried by the buffer to the test site. In the liquid conjugate system, a buffer-conjugate liquid subsystem is provided and applied to the first opening. The sorbent material then wicks the buffer-conjugate subsystem to the test site.

In another embodiment a dual path immunoassay test cell device for detecting the presence of a first ligand in a sample is provided with a first sorbent material defining a first horizontal flow path and a second sorbent material distinct from the first sorbent material and defining a second horizontal flow path, the first and second sorbent materials overlying one another at a test site. The first flow path has a first location for receiving a first solution, which, in the case of a liquid conjugate system is a conjugate solution, and which, in the case of a dry conjugate system is a buffer solution. Where a buffer solution is utilized, the first sorbent material is provided with a first (mobile) conjugate located downstream of the first location. The first conjugate includes a marker such as a colored latex or particle and a first interim binding agent such as (by way of example only) streptavidin or an anti-biotin antibody. The second flow path has a second location for receiving a second solution comprising a sample such as blood, urine, saliva, or other sample that has been optionally previously mixed with second-ligand binding molecules and, if desired, buffer and is optionally filtered to remove the second-ligand binding molecules and second ligand bound thereto prior to being applied as the second solution to the second location. The second flow path is provided with immobilized first-ligand binding molecules. The immobilized first-ligand binding molecules may include a second conjugate of latex particles (e.g., white latex) to which are bound antibodies or antigens and a second interim binding agent such as biotin. In this manner, when the sample includes the first ligand, the first-ligand binding molecules with the first ligand and second interim binding agent attached thereto are carried by the filtered sample solution to the test site along the second flow path. The test site which is located where the first and second sorbent materials overlie one another is provided with an immobilized binding agent which bind to the antigen or antibodies of the sample. Thus, the ligand with the second interim binding agent is bound at the test site, and when the first conjugate travels down the first flow path with the colored latex or particle and first interim binding agent, the interim binding agents will attach and keep the colored latex at the test site. A control line or site may be provided downstream from the test site.

In one aspect, where the first flow path is provided with a conjugate having a the second flow path is provided with immobilized first-ligand binding molecules with a second interim binding agent and the first test line is provided with a conjugate having a first interim binding agent, and sensitivity of the test is enhanced.

According to one method, a system for detecting the presence of a first ligand in a sample is provided and includes a test cell having a first sorbent material having a first location for receiving a buffer solution (in the case of a dry conjugate system) or a conjugate solution (in the case of a liquid conjugate system) with the first sorbent material defining a first horizontal flow path, and a second sorbent material having a second location for receiving a sample and defining a second horizontal flow path distinct from the first flow path, with the second sorbent material having a second-ligand binding molecules located downstream of the second location, and a test line or test site with immobilized first-ligand binding molecules such as antigens, antibodies, aptamers, nucleic acids, etc. located in a test zone at a junction of the first and second sorbent materials. If desired, a housing is also provided having a first opening for receiving the buffer or conjugate solution, a second opening for receiving the sample, and a viewing window above the test line. A sample of interest is provided to the second opening or location and permitted to migrate down to the test line over time. After a desired amount of time, a liquid such as a buffer solution is added to the first opening or location. If the first sorbent material is supporting a conjugate (i.e., in a dry conjugate system), the liquid can be simply a buffer solution. If the first sorbent material is not supporting a conjugate (i.e., in a liquid conjugate system), the liquid can be a buffer-conjugate liquid subsystem. In any event, after sufficient time to permit the first conjugate to migrate to the test site (and control site if provided), the test site (and control site if provided) is inspected in order to determine whether the sample is "positive" or not.

According to another method, a system for detecting the presence of a first ligand in a sample is provided and includes a test cell having a first sorbent material having a first location for receiving a buffer solution (in the case of a dry conjugate system) or a conjugate solution (in the case of a liquid conjugate system) with the first sorbent material defining a first horizontal flow path, and a second sorbent material having a second location for receiving a sample and defining a second horizontal flow path distinct from the first flow path with an optional filter, and a test line or test site with immobilized first-ligand binding molecules such as antigens, antibodies, aptamers, nucleic acids, etc. located in a test zone at a junction of the first and second sorbent materials. If desired, a housing is also provided having a first opening for receiving the buffer or conjugate solution, a second opening for receiving the sample, and a viewing window above the test line. A sample of interest is provided to a mixing chamber having second-ligand binding molecules and optional buffer. The sample is mixed with the second-ligand binding molecules (and buffer) and optionally filtered to remove the second-ligand binding molecules and second ligand attached thereto if the second flow path has no filter. The optionally filtered sample is provided to the second opening or location and permitted to migrate along the second flow path down to the test site. After a desired amount of time, a liquid such as a buffer solution is added to the first opening or location. If the first sorbent material is supporting a conjugate (i.e., in a dry conjugate system), the liquid can be simply a buffer solution. If the first sorbent material is not supporting a conjugate (i.e., in a liquid conjugate system), the liquid can be a buffer-conjugate liquid subsystem. In any event, after sufficient time to permit the first conjugate to migrate to the test site (and control site if provided), the test site (and control site if provided) is inspected in order to determine whether the sample is "positive" or not.

According to another method, a system for detecting the presence of a first ligand in a sample is provided and includes a test cell having a first sorbent material having a first location for receiving a buffer solution (in the case of a dry conjugate system) or a conjugate solution (in the case of a liquid conjugate system) with the first sorbent material defining a first horizontal flow path for a first conjugate having a marker and a first interim binding agent, and a second sorbent material having a second location for receiving a sample and defining a second horizontal flow path distinct from the first flow path with immobilized first-ligand binding molecules such as antibody or antigen bound to a second interim binding agent, and a test line or test site with immobilized binding agent located in a test zone at a junction of the first and second sorbent materials. If desired, a housing is also provided having a first opening for receiving the buffer or conjugate solution, a second opening for receiving the sample, and a viewing window above the test line. A sample of interest is optionally provided to a mixing chamber having second-ligand binding molecules and optional buffer. The sample may be mixed with the second-ligand binding molecules (and buffer) and filtered to remove the second-ligand binding molecules and second ligand attached thereto. The optionally filtered sample is provided to the second opening or location and may then interact with a second conjugate having a second interim binding agent as it migrates along the second flow path to the test site. After a desired amount of time, a liquid such as a buffer solution is added to the first opening or location. If the first sorbent material is supporting a first conjugate (i.e., in a dry conjugate system), the liquid can be simply a buffer solution. If the first sorbent material is not supporting a conjugate (i.e., in a liquid conjugate system), the liquid can be a buffer-conjugate liquid subsystem containing the first conjugate. In any event, after sufficient time to permit the second conjugate to migrate to the test site (and control site if provided), the test site (and control site if provided) is inspected in order to determine whether the sample is "positive" or not.

It will be appreciated that the systems can be used in conjunction with different types of samples such as blood, urine, saliva, etc. The sample may be diluted or mixed with buffer prior to being added through the second hole. Alternatively, in some cases, the sample may be added through the hole and then a diluent may be added through the same hole.

Objects and advantages will become apparent to those skilled in the art upon reference to the detailed description taken in conjunction with the provided figures.

DETAILED DESCRIPTION

Figure 1:
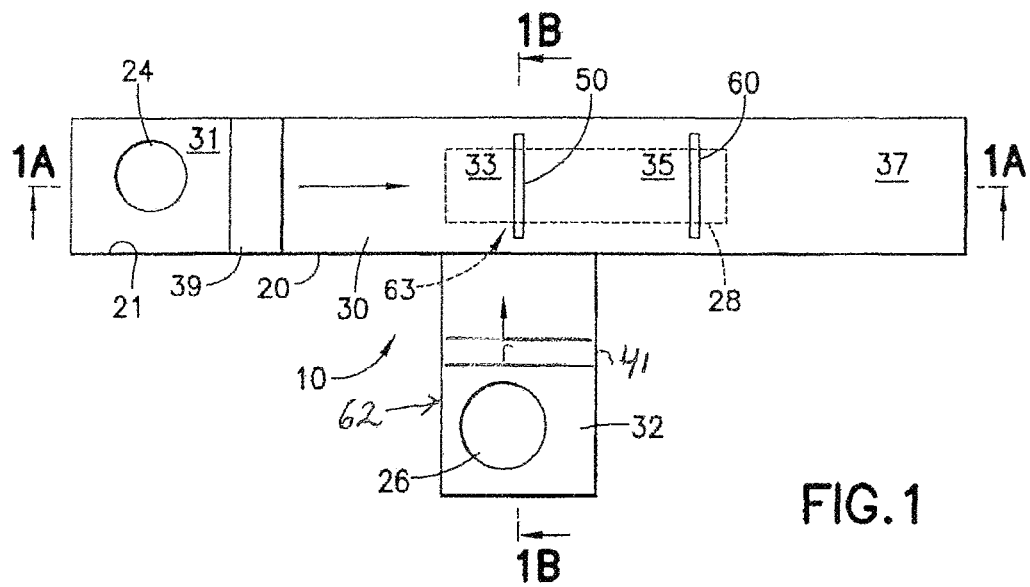
FIG. 1 is a top schematic view of a first embodiment.
Figure 1A:
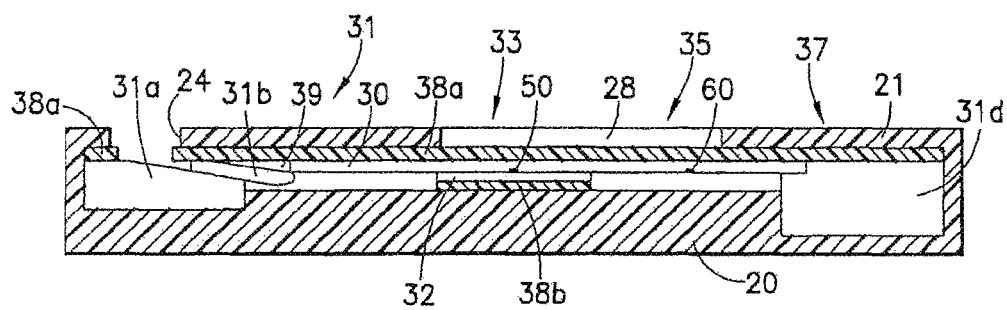
FIG. 1A is a cross-sectional view taken along line 1A-1A of FIG. 1.
Figure 1B:
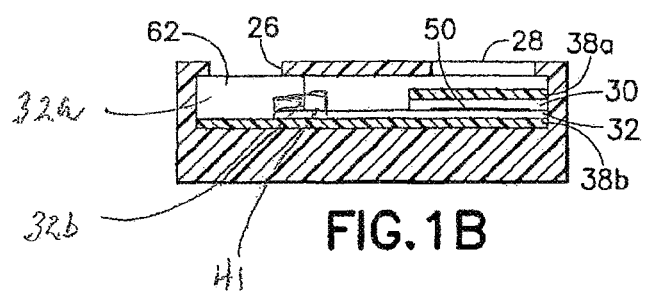
FIG. 1B is a cross-sectional view taken along line 1B-1B of FIG. 1.

Turning now to FIGS. 1, 1A and 1B, an immunoassay device test cell 10 for testing for the presence of a first ligand in a sample is provided and includes a housing 20 having a top wall 21 defining first and second holes 24, 26, and a window 28, and first and second sorbent or bibulous materials 30, 32 defining perpendicular horizontal or lateral flow paths in the housing. The first sorbent material 30 includes a plurality of zones and may be made from a plurality of materials. A first zone 31 (sometimes called a filter zone) is located at the first hole 24 and extends to a second zone 33 (sometimes called a test zone) which is located at the junction of a "T". The first zone 31 preferably includes a filter 31a, a pad 31b on or in which a conjugate 39 having desired antigens or antibodies with attached colored markers is deposited and immobilized, and a first portion of a thin membrane or sorbent or bibulous material 30 typically made from nitrocellulose with a plastic backing (not shown). In one embodiment, and by way of example only, conjugate 39 may be a gold sol conjugated to protein A. The first zone 31 is adapted to receive a buffer solution, to cause the buffer solution to contact the conjugate, thereby mobilizing the conjugate, and to wick the conjugate-carrying buffer solution to the second zone 33. The second (test) zone 33 includes a second portion of the thin membrane 30 which can be printed with a test line 50 having immobilized first ligand binding molecules such as antigens or antibodies (depending on whether the test cell is designed to test for the presence of antibodies or antigens) on the membrane as is well known in the art. The test line 50 may be seen through the window 28 of clear plastic provided in the housing. A third zone 35 (sometimes called a control zone) which includes a third portion of the thin membrane 30 may also be printed with a control line 60 typically containing antibodies to the conjugate antigens (or in some cases antibodies which will bind to conjugate antibodies, or even antigens which will bind to conjugate antibodies) as is well known in the art. Where the third zone 35 is provided, the window 28 extends above the control line 60. If desired, a fourth zone 37 (sometimes called a reservoir zone) may be provided as a wicking reservoir as is also well known in the art. The fourth zone 37 includes a relatively thicker absorbent paper. Preferably overlying all the zones is a thin, preferably transparent plastic film or card 38a having an adhesive which keeps the sorbent materials in place. The card 38a may be cut with an opening at hole 24 so that it does not block liquid access to the hole 24.

The second sorbent material 32 may also be made from a plurality of materials and include a plurality of zones. The first zone 62 (sometimes called a filter zone) includes a filter or pad 32a and a pad 32b on or in which second-ligand binding molecules are provided and immobilized, where the second ligand is different than but related to the first ligand, and a first portion of a thin membrane or sorbent or bibulous material 32 typically made from nitrocellulose with a backing (not shown). The second-ligand binding molecules may include antigens or antibodies or other molecules such as aptamers, nucleic acids, etc. that bind to ligands that are similar to but different than the first ligands. The second-ligand binding molecules may be provided as a conjugate 41 having desired antigens or antibodies with attached particles. The first zone 62 is located at the second hole 26 and extends to the second zone 63. The second zone 63 includes a second portion of the thin membrane 32 which is in contact with the second zone 33 of the first sorbent material 30. As is seen in FIGS. 1A and 1B, the first sorbent material 30 overlies the second sorbent material 32 such that the membranes are in contact with each other (as opposed to the backings contacting the membranes or each other), and such that the test line 50 is effectively located between the membranes. Thus, test line 50 could be printed on the second zone 63 of the second sorbent material 32 instead of, or in addition to the second zone 33 of the first sorbent material 30. If desired, a thin plastic film or card 38b having an adhesive which keeps the second sorbent material in place may be utilized. With the provided arrangement it takes time for the sample to travel from its application point to the second zone 63 and the test site, and application of sample to the second flow path does not immediately wet the test site.

In one embodiment the conjugate 41 on the conjugate pad 32b includes antigens conjugated with a particle that is not readily visible to the human eye against the background of the test area. In one embodiment, the particle is a white latex. One embodiment of a white latex is a 0.32 micron white latex bead available from Thermo Fisher Scientific, Inc., Holtsville, N.Y. The antigens of conjugate 41 are different than but are related to the antigens of test line 50. By way of example only, in an embodiment directed to detecting pandemic influenza ("flu"), the second conjugate includes antigens of at least one influenza ("flu") antigen (e.g., two different flu A antigens such as H1 and H3 flu antigens) and the test site is provided with immobilized antigen of at least the pandemic influenza antigen of interest which is different from but related to the at least one flu antigen of the immobilized conjugate 41. In another embodiment, the second conjugate includes antibodies conjugated with white latex and the test site 50 includes antibodies different than but related to the antibodies of the conjugate 41.

In one aspect, the second conjugate is used as a depleting mechanism that captures and thereby depletes antibodies related to the antibodies that are being detected at the test site. By way of example, where the test site includes a flu-B antigen for identifying the presence of a flu-B antibody in the sample, the second conjugate may be provided with one or more flu-A antigens; i.e., there may be a plurality of slightly different second conjugates. In this manner, flu-A antibodies in the sample that may otherwise be captured or retained at the test site (because of their structure which can be similar in many ways to the related flu-B antibodies) are generally captured by the second immobilized conjugate; i.e., the number of flu-A antibodies reaching the test site is depleted. As a result, the sensitivity of the test is increased. It will be appreciated that the test site could include a flu-A antigen for identifying the presence of a particular flu-A antibody in the sample, and the second conjugate may be provided with one or more flu-B antigens and one or more flu-A antigens that are different from but related to the particular flu-A antigen at the test site. Further, it will be appreciated that the test site may be provided with more than one test line, containing different flu antigens. Those flu antigens could include a plurality of flu-A antigens, a plurality of flu-B antigens, or one or more flu-A and one or more flu-B antigens. The second immobilized conjugate will be adjusted accordingly to include conjugate that will deplete those antigens that are related to the antigens of the test lines but are not the subject of the test.

In one aspect, the use of a white latex conjugate as the immobilized depleting conjugate reduces the visibility of the conjugate should it be loosened and travel with the sample to the test site and get captured at the test site. In another aspect, latex beads of a size larger than the pore size of the second migration path may be utilized in order to prevent movement of the conjugate along the second migration path.

Where standard-type nitrocellulose strips with a backing are utilized as the first and second membranes, the membranes can have different pore sizes. For example, if membrane 31 (for the first conjugate migration) has a 3µ pore size, and membrane 32 (for the sample migration) has a 15µ pore size, sample applied to membrane 32 will tend to migrate and stay in the sample membrane 32 and will tend not to migrate into the conjugate membrane 31.

The immunoassay of FIGS. 1, 1A and 1B is preferably utilized as follows. First, a sample (not shown) possibly containing antibodies (or antigens) is optionally diluted (e.g., with buffer) and provided to the second opening or hole 26. The sample does not immediately wet the test site but is allowed to take time to migrate from pad 32a to conjugate pad 32b and then from zone 61 of the second sorbent material 32 to its second zone 63 which is contact with the second zone 33 of the first sorbent material 30. If the sample is not first diluted, optionally, after providing the sample to hole 26, a measured amount of liquid such as a buffer solution may be added to hole 26 to help in the migration of the sample. Regardless, if the sample includes antigens or antibodies that react with the second conjugate 41 of conjugate pad 32b, those antigens or antibodies are captured by the conjugate 41 and are depleted from the sample before reaching the test line 50 which is printed atop the second zone 33 of the first sorbent material or infused therein. To the extent that the conjugate 41 loosens from the pad 32b and travels along membrane 32 down to the test site and is captured there, the conjugate 41 will not be particularly visible because the white latex particles will not be seen on the white background of the test site. Regardless, after a desired amount of time, by which time the antibodies (or antigens) in the sample (if present) will have had an opportunity to bind to the antigens (or antibodies) immobilized at the test line 50, a liquid such as a buffer solution (not shown) is added to the first opening 24. After another period of time, sufficient to permit the buffer solution to cause the conjugate to migrate to the test site 50 (and control site 60 if provided), and to bind with the antigens (or antibodies) of the sample that are captured at the test site 50 (if any), the test site (and control site 60 if provided) is inspected via window 28 in order to determine whether the sample is "positive" or not. Typically, a "positive" test indicating the presence of the antibody (or antigen) in the sample is obtained when both the test site 50 and the control site 60 show lines of color. A "negative" test indicating the lack of the presence of the antibody (or antigen) in the sample is obtained when only the control site 60 shows a line of color.

The use of the apparatus may be expedited by providing the housing with numbering and/or lettering to indicate that hole 26 is for receiving the sample (and optionally some buffer) and is to be used first, and that hole 24 is for receiving the buffer solution and is to be used second.

Those skilled in the art will appreciate that the immunoassay 10 functions as follows. Because the test line 50 is provided with antigens (or antibodies) immobilized on a membrane, if the test sample contains antibodies to the antigens (or antigens to the antibodies), the antibodies (or antigens) will bind themselves to the antigens (or antibodies) at the test line. Because the test sample passes through a conjugate pad 32b having immobilized second conjugate 41 with antigens (or antibodies) that are related to but different than the antigens (or antibodies) of the test line, related antibodies or antigens to those being tested, if present, will be captured by the conjugate 41 and held at the conjugate pad 32b, and when the test sample reaches the test line, the antibodies (or antigens) of the sample, if present, will bind to the antigen (or antibody) at the test line. Because the related antibodies (or antigens) are depleted, they will not reach the test line, and if they do, they will already be conjugated with a latex that will reduce their activity at the test site. Regardless, the test site will be more specific to the antibodies or antigens whose presence is to be detected. After the sample has reached the test site, the first conjugate 39 containing an antigen for the antibody (or antibody for the antigen) coupled to a colored marker is caused to migrate to the test line. If the test sample contains the antibodies (or antigens) which are now held at the test line 50, the antigen (or antibody) of the conjugate will bind itself to the antibodies (or antigens) and the colored marker will cause a colored line to appear at the test site 50. If the test sample does not contain antibodies (or antigens), the conjugate will not have the antibodies (antigens) to bind to at the test line 50, and no colored line will appear at the test site 50. On the other hand, because the control line 60 is provided with antibodies (or antigens), the antigens (or antibodies) of the conjugate will always bind to the antibodies (or antigens) in the control line 60, thereby causing a colored line to appear at the control site 60 if the conjugate reaches the control site 60. Thus, if sufficient buffer solution is provided to the test cell, a colored line should always appear at the control site 60, thereby providing a control for the test.

Figure 2A:
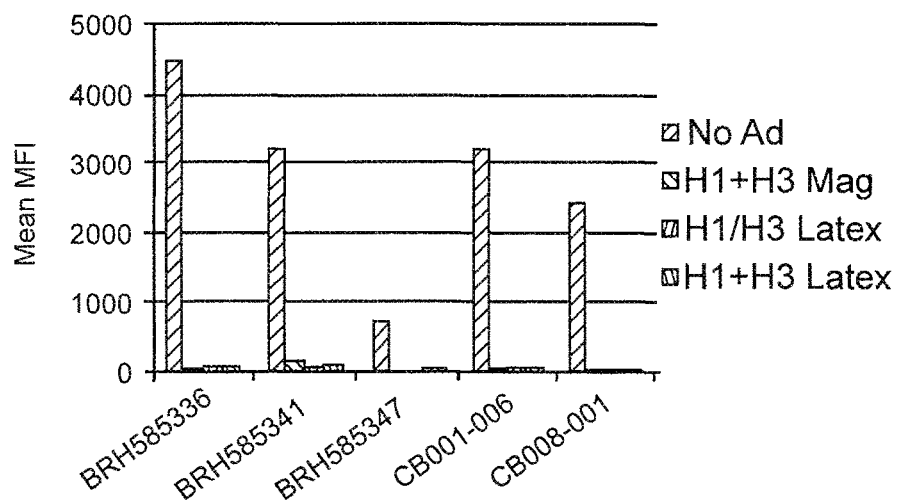
FIG. 2A is a chart comparing test results of the apparatus of FIG. 1 against the test results of a standard dual path platform apparatus and showing the depletion of non-pandemic flu antibodies by the apparatus of FIG. 1

Turning to FIG. 2A, it can be seen that the apparatus of FIGS. 1, 1A and 1B can provide improved test results relative to a standard dual path platform apparatus such as described and shown in previously incorporated U.S. Pat. No. 7,189,522. In particular, three sets of five test apparatus such as described above with reference to FIGS. 1, 1A and 1B were prepared with a second conjugate pad 32b provided with a conjugate 41 having H3 and H1 flu-A antigen conjugated with beads, and a DPP test line provided with Flu A antigens. One set of five apparatus utilized magnetic beads separately conjugated with H1 antigen and H3 antigen (H1+H3 Mag). A second set utilized latex beads separately conjugated with H1 and H3 antigen (H1+H3 Latex). A third set utilized latex beads with combined H1 and H3 conjugation (H1/H3 Latex). Similarly, a set of devices such as described and shown in previously incorporated U.S. Pat.

No. 7,189,522 were provided (No Ad) with a test line having the same flu-A antigens. Test samples from five different individuals having H3 antibodies were prepared and applied to the second flow paths of the sets of devices described above with reference to FIGS. 1, 1A and 1B and the set of devices of U.S. Pat. No. 7,189,522. After waiting for the samples to reach the test sites, buffer was added to the first migration path of each device to move the marker conjugate to the test sites. The intensity of the signals at each test site was measured and plotted. As seen in FIG. 2A, the test lines of the five standard dual path platform apparatus (No Ad) showed a relative intensity (with a digital reader) ranging from about 700 to well over 4000 compared to a relative intensity of nearly zero for the apparatus of FIGS. 1, 1A, and 1B utilizing the beads for the magnetic and latex beads. These test show that the apparatus of FIG. 1 is successful in depleting the flu-A antibodies by utilizing the flu-A antigen—particle conjugate in the flow path of the sample. Where white particles are utilized, to the extent that any flu-A antigen—particle conjugate was carried down to the test site and captured there, the white particle prevents the conjugate from being seen against the white background of card 38b over which the test line 50 is located. It should be appreciated that by depleting flu-A H1 and H3 (seasonal flu) with the latex conjugate system in the path of the sample, the sensitivity and specificity of the test with a test line for pandemic flu A will be increased because of the elimination of the cross-reactivity between the seasonal and pandemic flu A antigens.

In one embodiment, the conjugate in the sample flow path utilizes fragments or fractions of seasonal flu H1 and H3 conjugated to latex particles. The fragments are immunodominant portions of the particle that will not substantially cross-react with other flu antigens and are different from the H1 and H3 antibodies that might be used as capture antibodies at the test site in the membrane (the whole molecule of H1 and H3). As a result, when a test for pandemic flu is provided with a test line including pandemic flu antibodies, the H1 and H3 fragment conjugates will have minimal cross-reactivity with pandemic flu antigens resulting in a better detection of a pandemic flu at the test line.

Figure 2B:
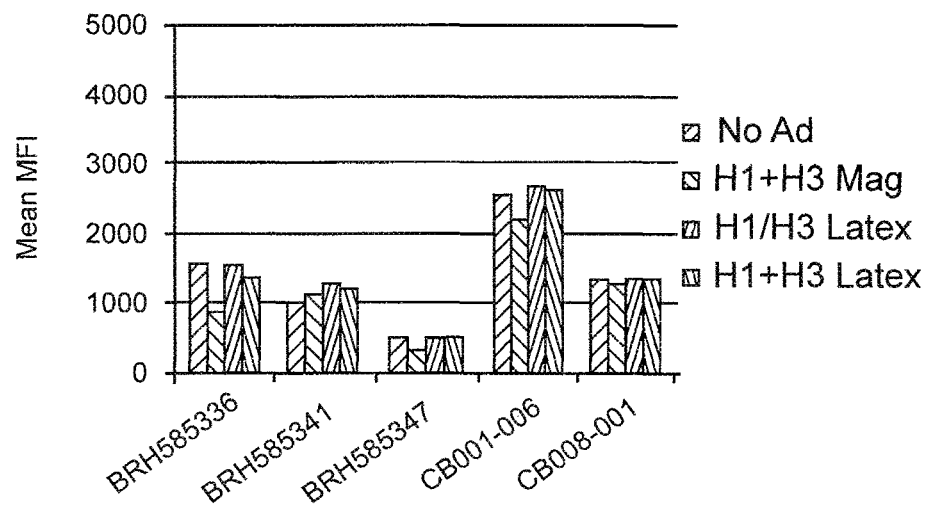
FIG. 2B is a chart comparing test results of the apparatus of FIG. 1 against the test results of a standard dual path platform apparatus and showing non-depletion of flu-B antibodies by the apparatus of FIG. 1.

Turning to FIG. 2b, other samples were prepared having flu-B/Bris antibodies. The samples were applied to a sets of the standard dual path platform apparatus such as described in previously incorporated U.S. Pat. No. 7,189,522 where the test line had flu-B/Bris antigen (No Ad) and to sets of devices such as shown in FIGS. 1, 1A and 1B where the second conjugate pad 32b was provided with a conjugate 41 having H1 and H3 flu-A antigens conjugated to beads, and a test line provided with flu-B/Bris antigens. As with tests of FIG. 2A, one set of apparatus utilized magnetic beads separately conjugated to H1 and H3 (H1+H3 Mag), a second set utilized 0.32 micron white latex beads separately conjugated (H1+H3 Latex), while a third set utilized the white latex beads with combined conjungation (H1/H3 Latex). As seen in FIG. 2B, the positive results at the test line of the apparatus 10 of FIG. 1 is just as strong as the test lines of the standard dual path platform apparatus showing that the conjugate 41 located in the second migration path did not interfere with the results, as the signals at the test lines were nearly the same for all tests of a particular sample. Taking FIGS. 2A and 2B together, it will be appreciated that the apparatus 10 of FIGS. 1, 1A, and 1B has higher sensitivity.

Figure 3:
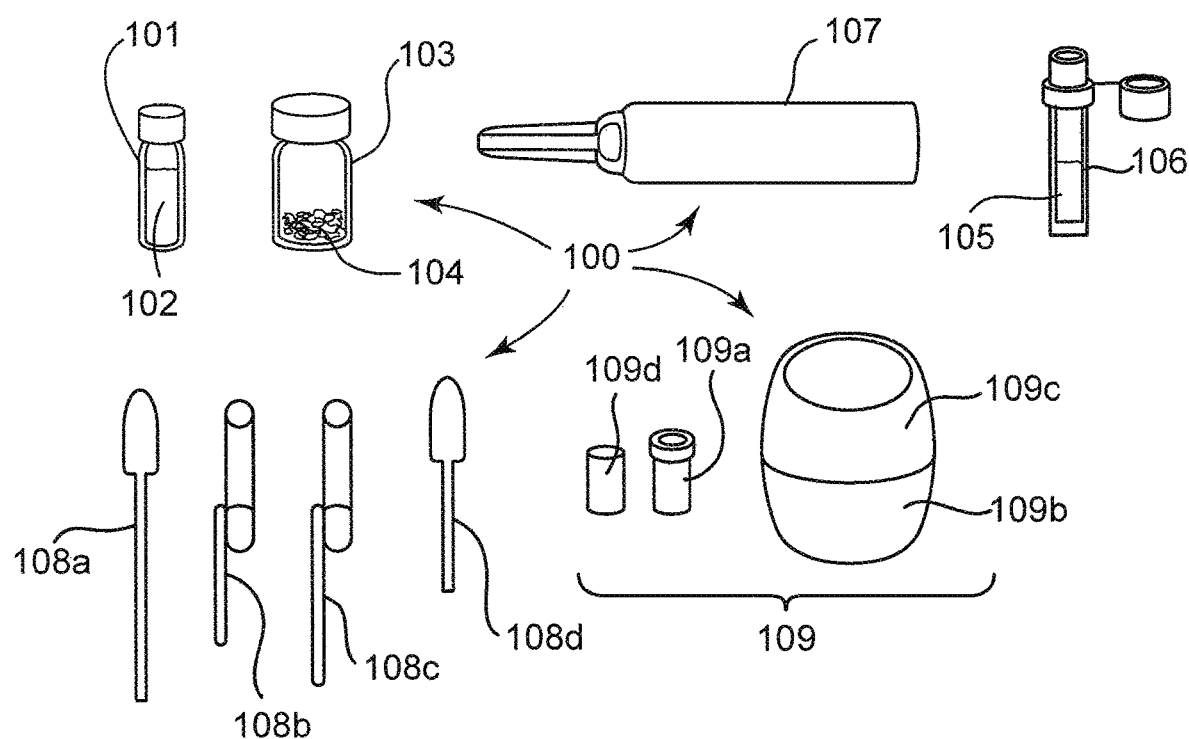
FIG. 3 is a diagram showing a kit including a water vial, a vial with conjugate, a vial with diluent, a blood collection and transfer device, three transfer pipettes, and a filter chamber.

Turning now to FIG. 3, a kit 100 is seen that includes a water vial 101 with water 102, a vial 103 with freeze dried latex conjugate 104, a diluent vial 105 with a diluent 106, a blood collection and transfer device 107, four transfer pipettes 108a, 108b, 108c, 108d, and a filter chamber assembly 109. It will be appreciated that the kit could have different numbers of elements. Thus, rather than separately maintaining water and freeze dried latex conjugate, a "wet" latex conjugate may be stored utilizing water and/or diluent. Likewise, rather than maintaining a vial of diluent, diluent may be provided as part of the "wet" latex conjugate. Also, rather than utilizing four transfer pipettes, fewer transfer elements may be utilized. In one embodiment, kit 100 may be used in conjunction with an immunoassay device test cell such as device 10 of FIGS. 1, 1A, and 1B. In another embodiment, kit 100 may be used in conjunction with other immnoassay devices such as ELISA (enzyme-linked immunosorbent assay). In another embodiment, kit 100 may be used in conjunction with an immunoassay device test cell such as described in previously incorporated U.S. Pat. No. 7,189,522.

More particularly, the water 102 in vial 101 may be mixed with the freeze dried latex conjugate 104 in vial 103 by using a pipette 108a and transferring the water to the latex vial. The vial 103 may be inverted multiple times in order to cause the freeze dried latex conjugate to be reconstituted. The reconstituted latex may be stored in a refrigerator if desired. In one embodiment, the dried latex conjugate is a conjugate of one or more flu antigens such as H1 and H3 with microbeads of latex. The latex beads may be of an easily visible color, e.g., blue.

When it is desired to test a sample, the sample, e.g., blood, may be obtained from a patient in a desired manner, e.g., a fingerstick, utilizing a blood collection and transfer device 107 such as a Minivette POCT manufactured by Sarstedt, Newton, N.C. The blood sample may be transferred into the diluent vial 105 containing a diluent 106 such as heparin or EDTA. The reconstituted latex conjugate may then be transferred into the diluent vial 105 by using a pipette 108b, and the blood and reconstituted latex conjugate may be mixed by inverting multiple times over a period of time and also giving antibodies in the blood an opportunity to be captured by the latex conjugate. After sufficient mixing and a sufficient period of time, the contents of the sample diluent vial 105 may then be transferred with pipette 108c to a filter chamber 109 such as a GE Healthcare Life Sciences Mini-UniPrep filter chamber comprising a filter 109a, compressor 109b, plunger 109c, and a tube 109d, although other filter mechanisms could be utilized. Using the hand compressor 109b of the filter chamber, the filter 109a can be plunged into the sample mixture, and the filtered sample can be collected in the tube 109d of the filter chamber. It will be appreciated that the filter is chosen to have pores that are smaller than the size of the latex conjugate beads. As a result, the conjugate beads (with captured antibodies, if any) are filtered out of the sample, and the sample (with antibodies that haven't been captured by the conjugate) with the previously added diluent and water will be caught in the tube 109d. Thus, while the contents of the sample diluent vial 105 that were transferred to the filter chamber 109 may have appeared to be dark blue (due to the blue latex conjugate and the blood), the contents of the tube 109d should be light red (the color of diluted blood). Regardless, it will be appreciated that the ligands that are related to but not the same as the ligands of interest will have been removed from the sample.

The contents of tube 109d are then transferred by pipette 108d and used in conjunction with an immunoassay device. In one embodiment, the immunoassay device is an otherwise prior art type device such as ELISA (enzyme-linked immunosorbent assay) or a LUMINEX assay sold by Thermo Fisher Scientific, Holtsville, N.Y. When provided with a sample that is processed in this manner, the results of the ELISA and the LUMINEX devices are enhanced. In another embodiment, the immunoassay device to which the contents of tube 109d are transferred is an immunoassay device test cell such as described in previously incorporated U.S. Pat. No. 7,189,522 such as by applying a selected amount of the contents to the (second) location for receiving the liquid sample, waiting for the liquid sample to reach the test site via the second migration path, and then applying buffer or a buffer—conjugate subsystem to the first location to cause a conjugate to reach the test site via the first migration path. When provided with a sample that is processed as previously described, the results of the device described in previously incorporated U.S. Pat. No. 7,189,522 are enhanced.

In another embodiment, rather than utilizing a kit 100 with elements such as a water vial, a vial with freeze dried latex conjugate, a diluent vial, a filter chamber assembly, etc., the kit includes a conjugate which may be maintained in a wet form with or without buffer, or may be maintained in a freeze-dried conjugate format which may be reconstituted with water and/or a buffer solution. In one embodiment, the latex conjugate comprises white latex beads with antibodies or antigens conjugated thereto. The sample and conjugate are mixed together to permit the conjugate to deplete interfering antigens or antibodies. The mixed sample and conjugate may then be applied to an immunoassay device test cell such as described in previously incorporated U.S. Pat. No. 7,189,522 such as by applying a selected amount of the contents to the (second) location for receiving the liquid sample, waiting for the mixed sample and conjugate to reach the test site via the second migration path, and then applying buffer or a buffer—conjugate subsystem to the first location to cause a conjugate to reach the test site via the first migration path. When provided with a sample that is processed as previously described, the results of the device described in previously incorporated U.S. Pat. No. 7,189, 522 are enhanced.

Figure 4A:
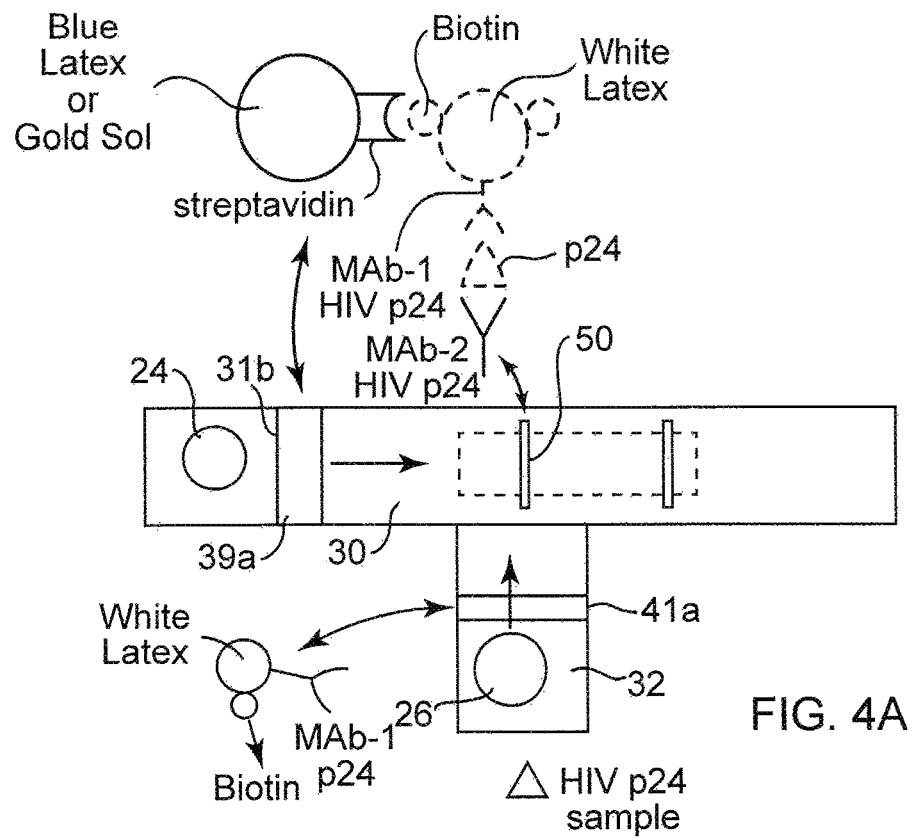
FIG. 4A is a diagram depicting a first alternative embodiment.
Figure 4B:
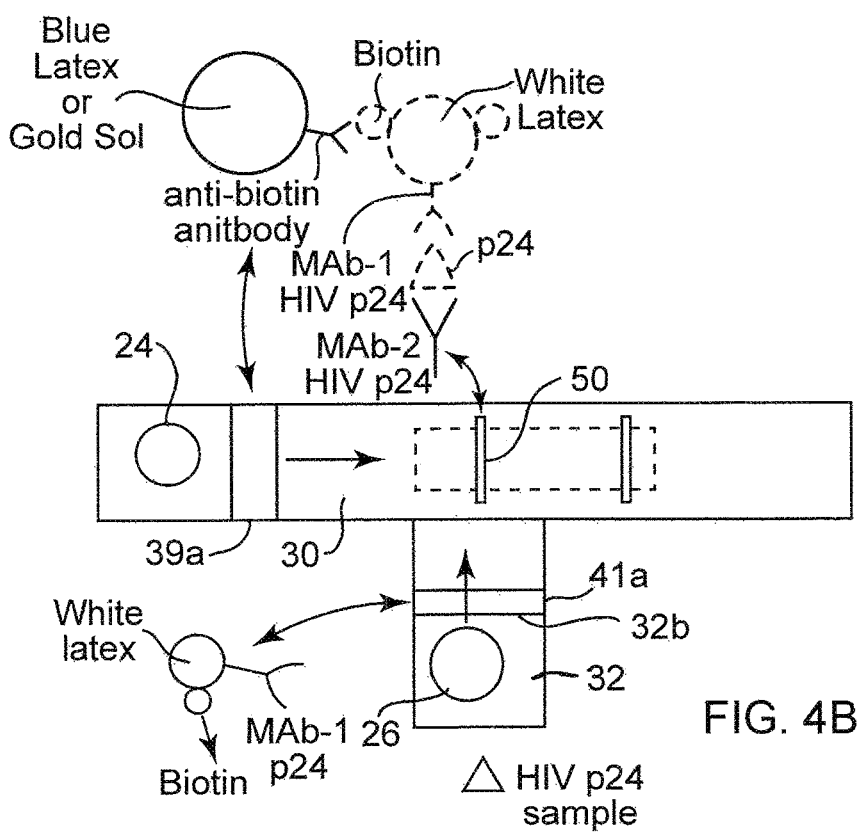
FIG. 4B is a diagram depicting a second alternative embodiment.
Figure 4C:
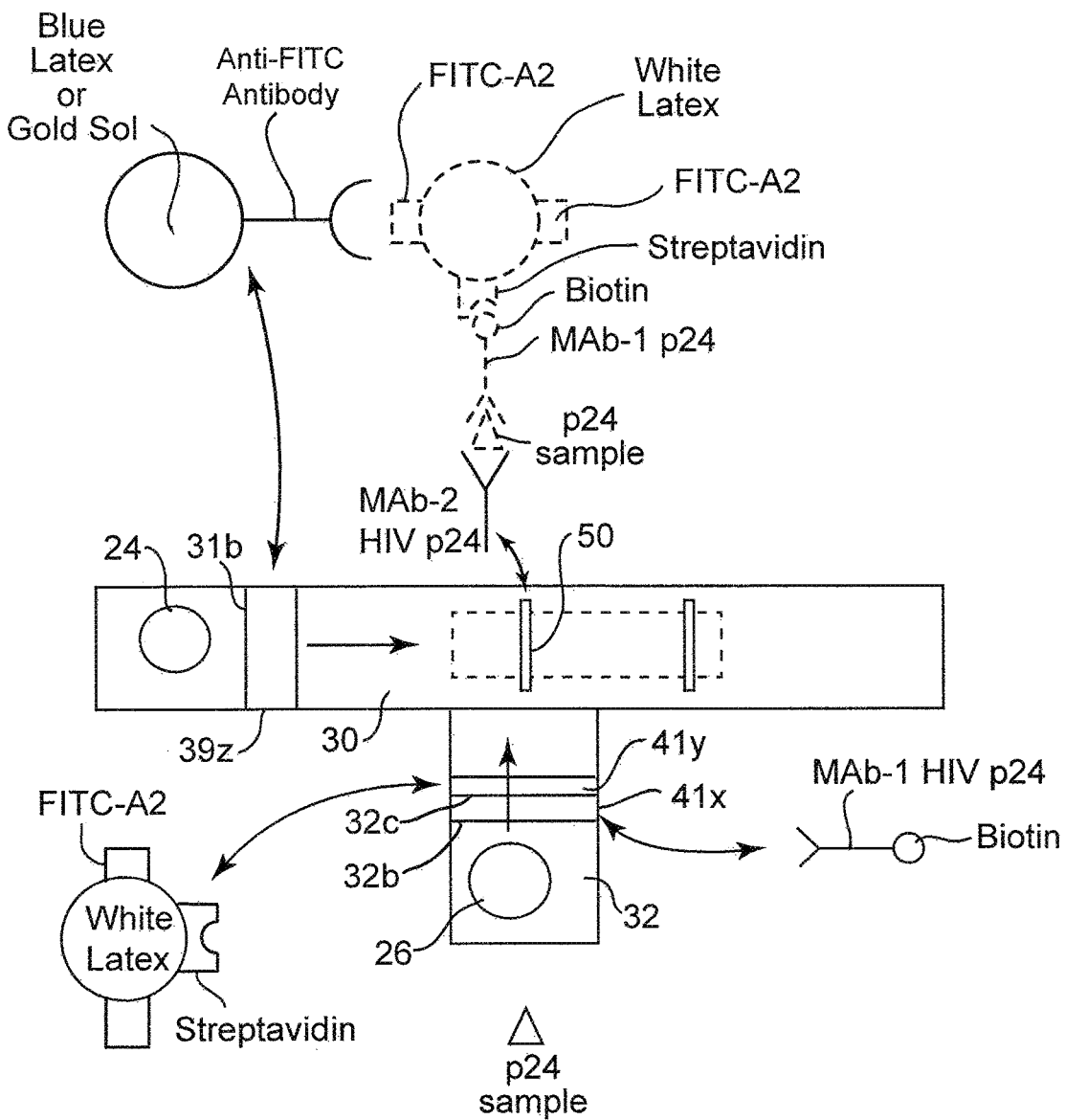
FIG. 4C is a diagram depicting a third alternative embodiment.

Turning to FIGS. 4A-4C, additional embodiments are provided that result in an apparatus having an enhanced test signal. FIGS. 4A-4C are described with reference to HIV test devices although they are not limited thereto. The embodiments of FIGS. 4A and 4B are similar to that of FIGS. 1, 1A, and 1B except that the conjugates provided on pads 31b and 32b are different, and the immobilized test line antigen is an HIV antibody rather than a flu antibody. More particularly, in FIG. 4A, conjugate 41a in the sample migration path 32 includes a latex particle (e.g., a white latex) to which a MAb-1 p24 antibody and a first interim binding agent (e.g., biotin antigen) are conjugated. The test line 50 is provided with a monoclonal anti-HIV antibody protein (MAb-2 p24). The buffer-conjugate subsystem of the first migration path 30 is provided with a conjugate 39a including a marker (e.g., blue latex or gold sol) and a second interim binding agent (e.g., streptavidin) conjugated thereto that is chosen to bind to the first interim binding agent. With the provided system, when a sample containing HIV p24 antigen is added to the test apparatus through hole 26, the HIV p24 antigen in the sample will bind to the MAb-1 p24 of the conjugate, and the sample with the antigen of interest bound to the conjugate will travel to the test line 50 where the p24 antigen of the sample will be caught by the MAb-2 p24 antibody at the test line. When buffer is added to the first sorbent strip through hole 24, the marker conjugate will move to the test line where the first interim binding agent will bind with the second interim binding agent, and the marker will appear at the test line.

The embodiment of FIG. 4B is very similar to the embodiment of FIG. 4A, except that instead of the second interim binding agent of conjugate 39a being a tetrameric protein such as streptavidin, the second interim binding agent is an anti-biotin antibody. As a result, where the sample contains HIV p24 antigen, at the test line, the HIV p24 antigen will be retained at the test line by the MAb-2 p24 antibody of the test line, and the marker conjugate will bind to the first conjugate because the antibiotin antibody will bind to the biotin that is part of the first conjugate as seen in FIG. 4B The embodiment of FIG. 4C is likewise similar to the embodiments of FIGS. 4A and 4B, except that a double interim binding arrangement is utilized. More particularly, the second sorbent material 32 is provided with a pad 32c in addition to pad 32b. In one embodiment, pad 32b is provided with MAb-1 HIV p24 antigen conjugated with biotin 41x with the biotin acting as a first interim binding agent of a first pair, and pad 32c is provided with particles such as a white latex particles conjugated with streptavidin and a secondary antigen such as FITC-A2 (fluorescein isothiocyanate) 41y. The streptavidin of particles 41y act as a second interim binding agent of a first pair, and the FITC-A2 acts as a first interim binding agent of a second pair. Pad 31b is provided with a conjugate 39z having a marker to which is conjugated an anti-FITC antibody which acts as a second interim binding agent of a second pair. With the provided arrangement, if the sample contains a p24 antigen, when the sample is added to the second sorbent material 32, the p24 antigen will attach to the MAB-1 HIV p24 antibody with biotin at pad 32b. As the sample progresses along its migration path to pad 32c, the biotin will bind to the streptavidin of the conjugate 41y; i.e., the first and second interim binding agents of the first pair bind together, and the complex of the p24 antigen—MAB-1 HIV p24 antibody with biotin—streptavidin/white latex/FITC antigen conjugate 41y will move to the test site that includes MAB-2 HIV p24 antibody. At the test site, the p24 antigen of the sample will bind to the MAB-2 HIV p24 antibody of the test site, and the entire previously—described complex will be held at the test site. When buffer is then added to the first migration path and marker-anti-FITC antibody conjugate is moved to the test site, the anti-FITC antibody will bind to the FITC-A2 being held at the test site; i.e., the first and second interim binding agents of the second pair bind together. As a result, the marker will be held at the test line and provide a positive test result.

The embodiments of FIGS. 4A-4C may all be used in conjunction with a sample being provided directly to the apparatus or with a sample such as the previously described sample contained in tube 109d which has resulted from a sample having been previously mixed with a depletion conjugate for antigens or antibodies different from but related to the antigen or antibody of interest and then filtered. In all cases, the molecules and conjugates on pads 32b and 31b, and 32c (if present) are appropriately selected, as are the molecules on the test line 50 and the freeze-dried depletion conjugate 104.

Figure 5A:
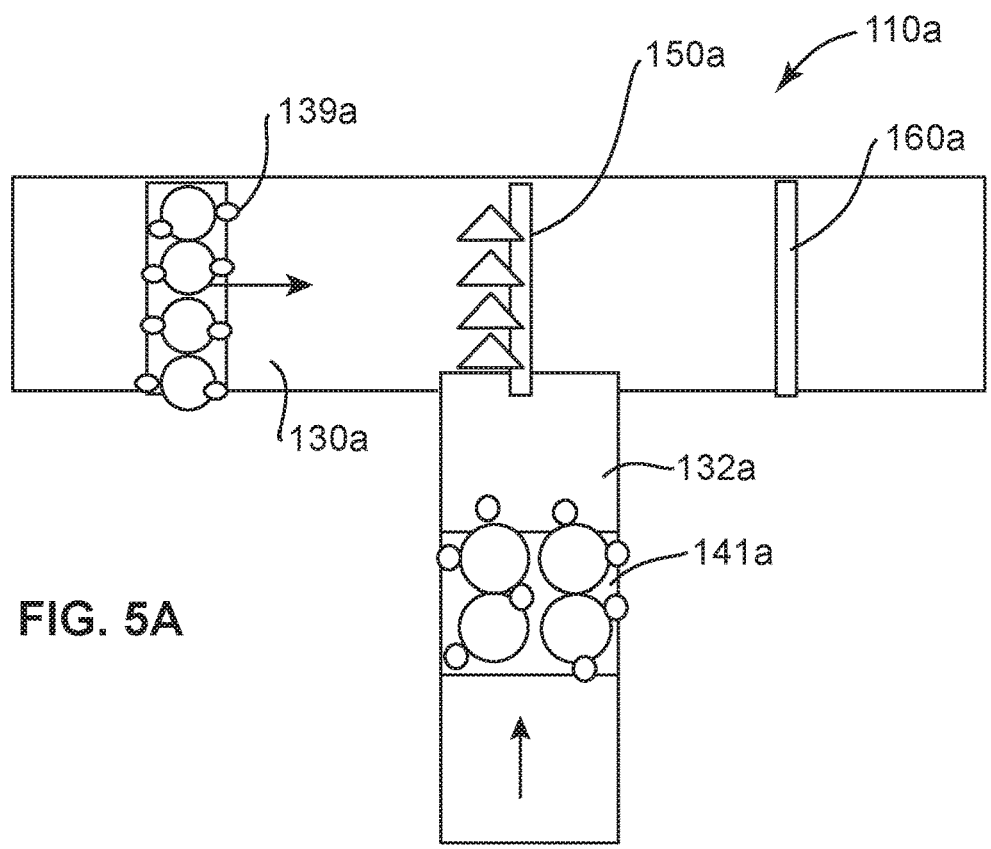
FIGS. 5A-5D are diagrams depicting embodiments of Dengue immunoassay device test cells.
Figure 5B:
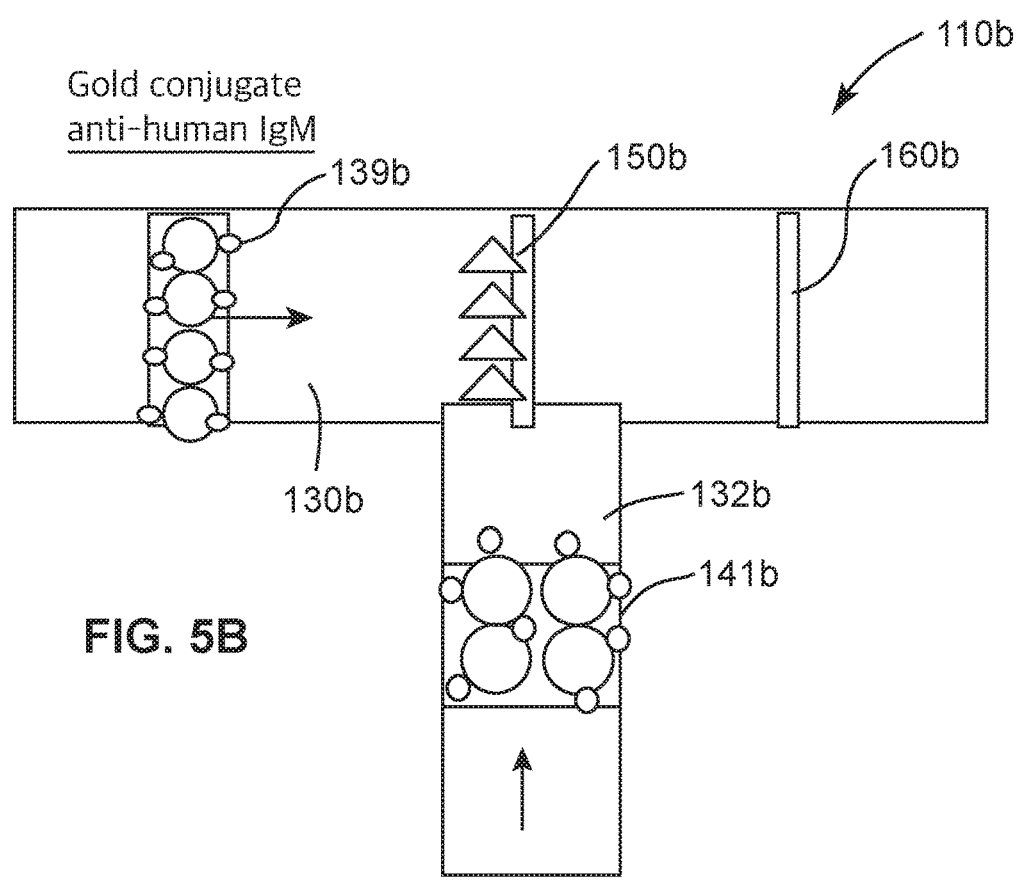
Figure 5C:
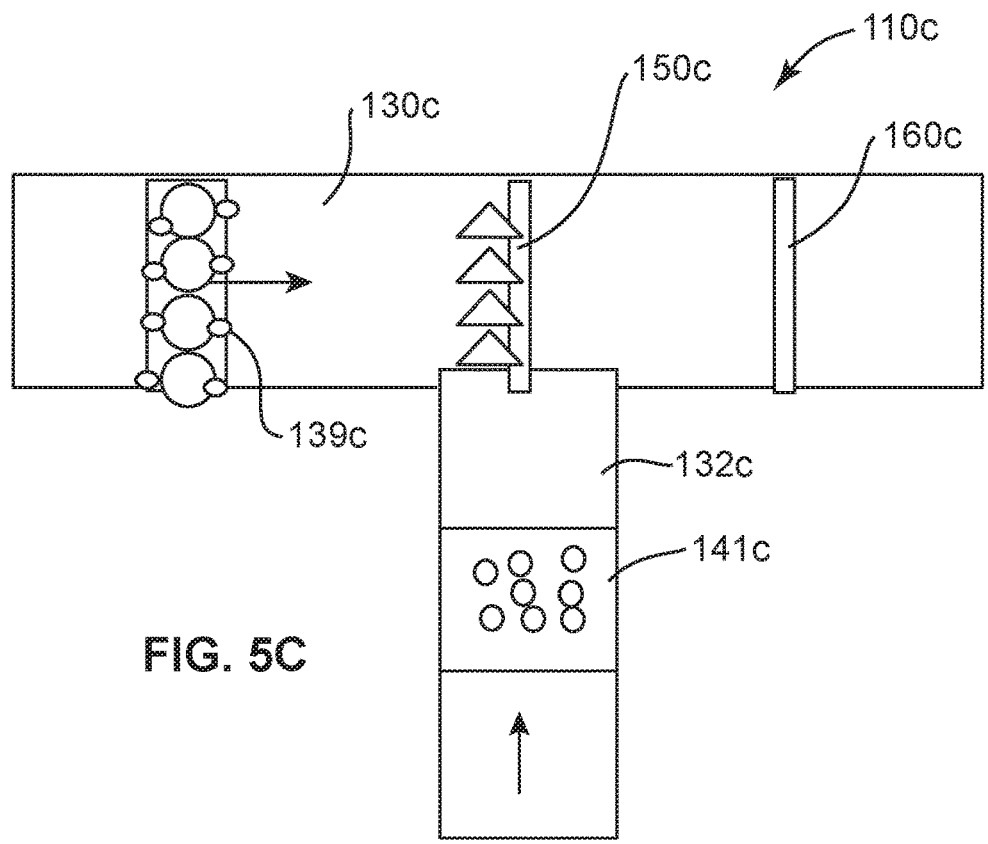
Figure 5D:
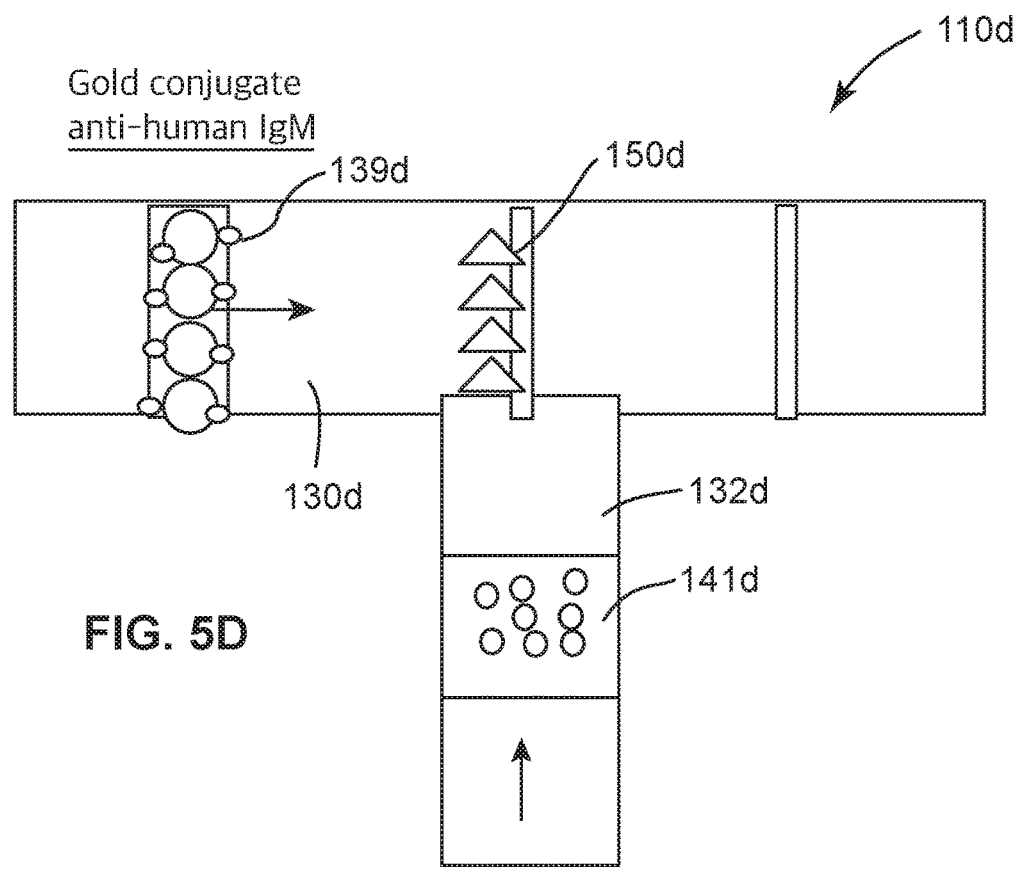

Turning now to FIGS. 5A-5D, four different embodiments of immunoassays for detecting the flavivirus/arbovirus Dengue are provided. FIGS. 5A and 5B are respectively directed to IgG and IgM Dengue immunoassays that utilize latex particles in a depletion zone, whereas FIGS. 5C and 5D are respectively directed to IgG and IgM Dengue immoassays that do not utilize latex particles in the depletion zone. In all four embodiments of FIGS. 5A-5D, the depletion zone are provided with recombinant antigens and/or synthetic peptide antigens of at least one of the Zika, West Nile and Yellow fever flaviviruses, which are related to, but are different than the Dengue flavivirus. In some cases, two, or three of those flaviviruses are provided in the depletion zone.

It should be appreciated that Dengue, Zika, West Nile, and Yellow fever are considered related because they are a genus of virus in the family Flaviviridae which are positive, single-stranded, enveloped RNA viruses that have significant antigenic cross-reactivity as they share antigenic sites on a fusion loop of a domain (Domain II) of their envelope proteins of their lipid membranes. Thus, it should be appreciated that all flaviviruses are antigenically related to various degrees, and immunological cross-reactions have been implicated not only in cross-protection but, under certain conditions, also in infection enhancement phenomena that may exacerbate disease in humans and/or facilitate vector transmission.

As will be described in more detail hereinafter, in some embodiments of the Dengue immunoassays of FIGS. 5A-5D, the depletion zones also include recombinant antigens to one or more alphaviruses (of the family Togaviridae) such as Chikungunya. Alphavirus were originally classified as flaviviruses because of the cross-reactivity or their serocomplexes, but were later found to be of a separate, albeit related family. All alphaviruses share antigenic sites on the capsid and on a fusion loop of a domain (Domain II) of their envelope proteins (as do the flaviviruses).

Alphavirus RNA is a single 42S strand of approximately $4 \times 10^6$ daltons that is capped and polyadenylated. Flavivirus RNA is a single 40S (ca. 10.9 kilobases) positive-sense strand and is capped at the 5' end, but, unlike alphaviruses, has no poly A segment at the 3' end. The flavivirus virion has a single capsid protein (C) that is approximately 13,000 daltons. The envelope consists of a lipid bilayer, a single envelope protein (E) of 51,000-59,000 daltons, and a small nonglycosylated protein (M) of approximately 8,500 daltons.

Because flaviviruses (and alphaviruses) are cross-reactive, serological diagnostic assays for detections of a single flavivirus or alphavirus are found to have lower specificity than desired; whereas high specificity is important to avoid false positive results. False positive results can lead to misdiagnosis and improper treatment or vaccination. Among flaviviruses, cross-reactivity (and resultingly, false positive test results) can be as high as 25%-40%.

In addition, and according to one aspect, serological assays (IgG detection) have been used for vaccine monitoring as the immune-status of a patient prior to vaccination can have impact in the efficacy of the vaccine. Therefore, a diagnostic test for the IgG of a particular flavivirus or alphavirus can provide additional information regarding the desirability of a patient getting a vaccine or not. For example, there exist studies which indicate that a prior flavivirus infection (such as Dengue) can improve the efficacy of the Dengue vaccine with the prior antibody titer effectively acting as a first dose of the vaccine. Accordingly, a diagnostic IgG Dengue test can discriminate a patient with a prior Dengue IgG infection from a patient who never had such an infection. If there is a potential risk associated with vaccination of a non-previously-infected patient, then a highly specific test could help avoid the vaccination risks.

Turning now to FIG. 5A, a highly specific immunoassay device test cell 110a for testing for the presence of Dengue IgG in a sample is provided and includes first and second sorbent or bibulous materials 130a, 132a defining perpendicular horizontal or lateral flow paths. Test cell 110a is substantially the same as immunoassay device test cell 10 of FIGS. 1, 1A, and 1B and includes the same elements thereof, except for the specifics of the depletion zone located on or in the second sorbent material 132a (of the second flow path), and the specifics of the test line 150a located at the intersection of the first and second sorbent materials. Thus, as with test cell 10, test cell 110a may include a control line 160a, a housing (not shown), the sorbent materials 130a, 132a may include various zones, the marker conjugate 139a of test cell 110a is provided with visible particles (e.g., gold sol) conjugated with Protein A or anti-human IgG (which both bind human IgG), etc. However, test cell 110a is specific for testing Dengue IgG, so the test line 150a includes immobilized Dengue antigens, while the depletion zone is provided with second conjugates 141a of particles (e.g., latex) conjugated to one or more antigens against viruses that are different than but related to and cross-reactive with Dengue. In one embodiment, the conjugates 141a of the depletion zone are conjugates of a latex with antigens of one or more of Zika, Chikungunya, West Nile, and Yellow fever. In another embodiment, the conjugates of depletion zone 141a are conjugates of a latex with antigens of two or more of Zika, Chikungunya, West Nile, and Yellow fever. In another embodiment, the conjugates 141a of the depletion zone are conjugates of a latex with antigens of three or more of Zika, Chikungunya, West Nile, and Yellow fever. In another embodiment, the conjugates 141a of the depletion zone are conjugates of a latex with antigens of at least all four of Zika, Chikungunya, West Nile, and Yellow fever. In embodiments, the antigens are specific to each of their respective virus antibodies. In some embodiments, the specific antigens are one or more of recombinant antigens, synthetic peptides, and lysate antigens. Accordingly, the second conjugate is used as a depleting mechanism that captures and thereby depletes antibodies different than but related to the Dengue antibodies that are to be detected at the test site.

In one embodiment (as in the embodiments previously described with respect to test cell 10), the particles of the second conjugates 141a in the depletion zone are not readily visible to the human eye against the background of the test area, such as conjugates using white latex particles. In one embodiment, the second conjugates are immobilized in the depletion zone so that they, and the antibodies that attach themselves to the conjugate do not travel with the sample to the test line. In one aspect, the use of a white latex conjugate as the immobilized depleting conjugate reduces the visibility of the conjugate should it be loosened and travel with the sample to the test site and get captured at the test site. In another aspect, latex beads of a size larger than the pore size of the second migration path may be utilized in order to prevent movement of the conjugate along the second migration path.

In one aspect, the second conjugate is used as a depleting mechanism that captures and thereby depletes antibodies related to the antibodies that are being detected at the test site.

The immunoassay device test cell 110b of FIG. 5b is provided for testing for the presence of Dengue IgM in a sample and includes first and second sorbent or bibulous materials 130b, 132b defining perpendicular horizontal or lateral flow paths. Test cell 110b is substantially the same as immunoassay device test cell 110a of FIG. 5a and includes the same elements thereof, except for the specifics of the conjugate 139b in the conjugate zone located on or in the first sorbent material 130b. Thus, as with test cell 110a, test cell 110b may include a test line 150b with immobilized Dengue antigen, control line 160b, a housing (not shown), and the sorbent materials 130b, 132b may include various zones. In addition, the specifics of the depletion zone located on or in the second sorbent material 132b (of the sample flow path) may be the same as depletion zone of test cell 110a. However, because the test cell 110b is specific for testing Dengue IgM, the marker conjugate 139b of test cell 110b is provided with anti-human IgM antigen (as opposed to anti-human IgG) that are conjugated to visible particles (e.g., gold sol). As a result, as described in more detail hereinafter, the presence of Dengue IgM antibodies in the sample is detected at the test line 150b even in the presence of antibodies from interfering (cross-reactive) flaviviruses and/or alphaviruses.

The immunoassay device 110c of FIG. 5C is similar to the device 110a of FIG. 5A and includes the same elements (e.g., sorbent strips 130c, 132c, test line 150c, control line 160c) with the exception that the depletion zone does not utilize a conjugate, but instead utilizes antigens 141c of one or more of Zika, Chikungunya, West Nile, and Yellow fever which may be mixed with a stabilizer/blocker and sprayed on the sorbent strip 132c. The antigens may be immobilized if desired. As a result, as described hereinafter in more detail, Dengue IgG is detected at the test line 150c even in the presence of interfering (cross-reactive) flaviviruses and/or alphaviruses, as the interfering antibodies are depleted by the antigens in the depletion zone. Even if the interfering flaviviruses and/or alphaviruses travel with the sample (because the antigens 141c in the depletion zone are not immobilized), their reactive sites will have been occupied by the specific antigens of the depletion zone so that they will not react (i.e., be captured) at the test line 150c.

The immunoassay device 110d of FIG. 5D is similar to the device 110b of FIG. 5B and includes the same elements (e.g., sorbent strips 130d, 132d, anti-human IgM conjugate 139d, test line 150d, control line 160c) with the exception that the depletion zone does not utilize a conjugate, but instead utilizes antigens 141d of one or more of Zika, Chikungunya, West Nile, and Yellow fever which may be mixed with a stabilizer/blocker and sprayed on the sorbent strip 132d. As a result, as described hereinafter in more detail, Dengue IgM is detected at the test line 150d even in the presence of interfering (cross-reactive) flaviviruses and/or alphaviruses, as the interfering antibodies are depleted by the antigens of the depletion zone.

The immunoassays of FIGS. 5A-5D may be utilized as follows. First, a sample (not shown) possibly containing Dengue antibodies is optionally diluted (e.g., with buffer) and provided to the second sorbent strip. The sample does not immediately wet the test site but is allowed to take time to migrate from its location of application to the depletion zone, and then to the test site. If the sample is not first diluted, optionally, after providing the sample to the second sorbent strip, a measured amount of liquid such as a buffer solution may be added to the second sorbent strip to help in the migration of the sample. Regardless, if the sample includes antigens or antibodies that react with the antigens in the depletion zone, those antibodies are captured at the depletion zone and are depleted from the sample before reaching the test line. To the extent that the depletion zone antigens are not immobilized, or loosen from the sorbent strip and travels down to the test site, many of the reactive sites on the antibodies of the related flaviviruses and/or alphaviruses are occupied with depletion zone recombinant antigens so that they will not bind to the Dengue antigen at the test line. Conversely, to the extent Dengue antibodies are present in the sample, they will generally not be depleted significantly by the specific antigens in the depletion zone, but will travel down to the test line and bind to the Dengue antigens immobilized at the test line. A sufficient time after application of the sample to the second sorbent strip of the immunoassay, a liquid such as a buffer solution is added to the first sorbent strip. The solution is added to a location which permits it to cause the conjugate on the first sorbent strip to migrate to the test site (and control site, if provided), and to bind with the antibodies of the sample (if present) that are captured at the test site. The test site and control site are then inspected in order to determine whether the sample is "positive" or not. Typically, a "positive" test indicating the presence of the antibody in the sample is obtained when both the test site and the control site show lines of color. A "negative" test indicating the lack of the presence of the antibody in the sample is obtained when only the control site shows a line of color.

The use of the immunoassay apparatus may be expedited by providing a housing for the sorbent strip, with the housing having holes and numbering and/or lettering to indicate that one hole in the housing is for receiving the sample (and optionally some buffer) and is to be used first, and that another hole is for receiving the buffer solution (that moves the marker conjugate) and is to be used second.

Those skilled in the art will appreciate that the immunoassays of FIGS. 5A-5D function as follows. Because the test line is provided with antigens immobilized on a membrane, if the test sample contains antibodies to the antigens, the antibodies will bind themselves to the antigens at the test line. Because the test sample passes through a depletion zone having specific recombinant antigens that are related to but different than the antigens of the test line, related antibodies to those being tested, if present, will be captured by the recombinant antigens and, if immobilized, held at the depletion zone. When the test sample reaches the test line, the antibodies of the sample, if present, will bind to the antigen at the test line. Because the related antibodies are depleted, they will not reach the test line (if immobilized), and if they do, they will already attached to antigens that will reduce their activity at the test site. Regardless, the test site will be more specific to the antibodies whose presence is to be detected. After the sample has reached the test site, the marker conjugate is caused to migrate to the test line. If the test sample contains the antibodies which are now held at the test line, the conjugate will bind itself to the antibodies of the sample and the colored marker will cause a colored line to appear at the test site. If the test sample does not contain antibodies of interest, the conjugate will not bind to at the test line, and no colored line will appear at the test site. Also, if IgG antibodies are captured at the test line, but the test is for IgM (as in the embodiments of FIGS. 5B and 5D), the anti-human IgM marker conjugate will not bind to the IgG antibodies and a colored line will not appear at the test line. On the other hand, because the control line is provided with antibodies to which the conjugate will bind, the conjugate will always bind to the antibodies in the control line, thereby causing a colored line to appear at the control site if the conjugate reaches the control site. Thus, if sufficient buffer solution is provided to the test cell, a colored line should always appear at the control site, thereby providing a control for the test.

According to one embodiment, any specific antigens may be utilized in the depletion zone, including, but not limited to recombinant antigens, synthetic peptides, and lysates that are specific to the cross-reacting flavivirus and/or alphavirus antigens. The synthetic peptides, lysates and recombinant antigens may be provided either as part of a conjugate or in conjunction with stabilizer/blockers.

Figure 6A:
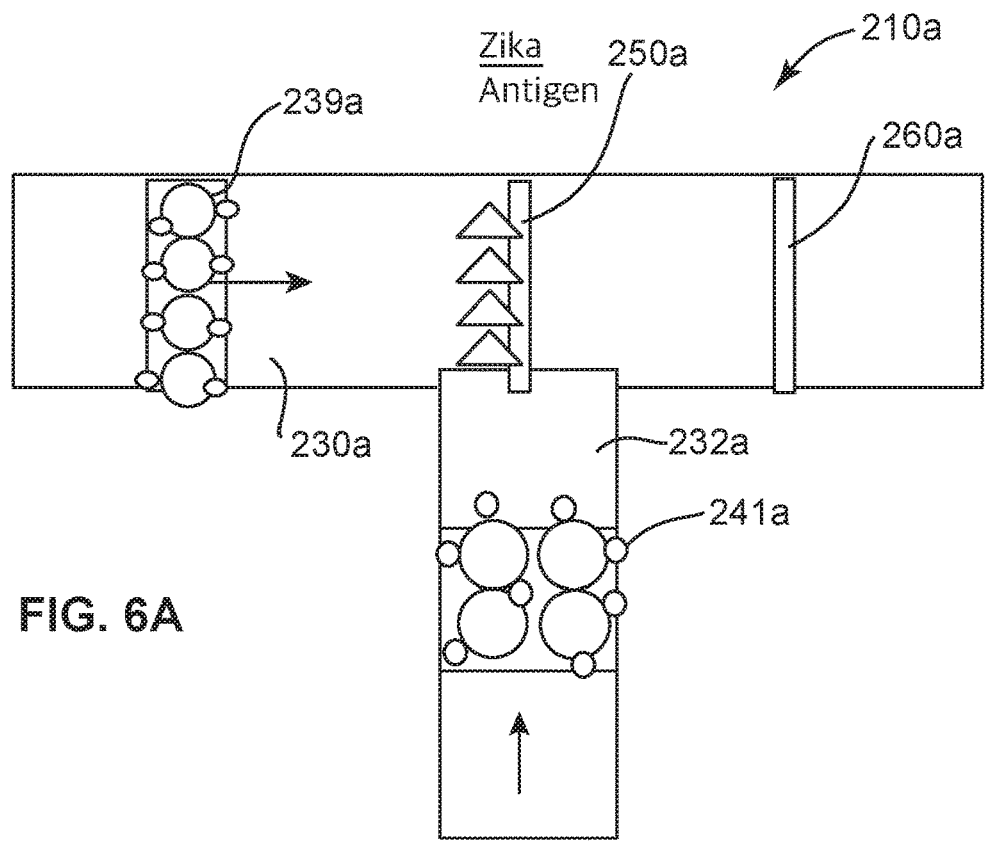
FIGS. 6A-6B and 7A-7B are diagrams depicting embodiments of Zika immunoassay device test cells.
Figure 6B:
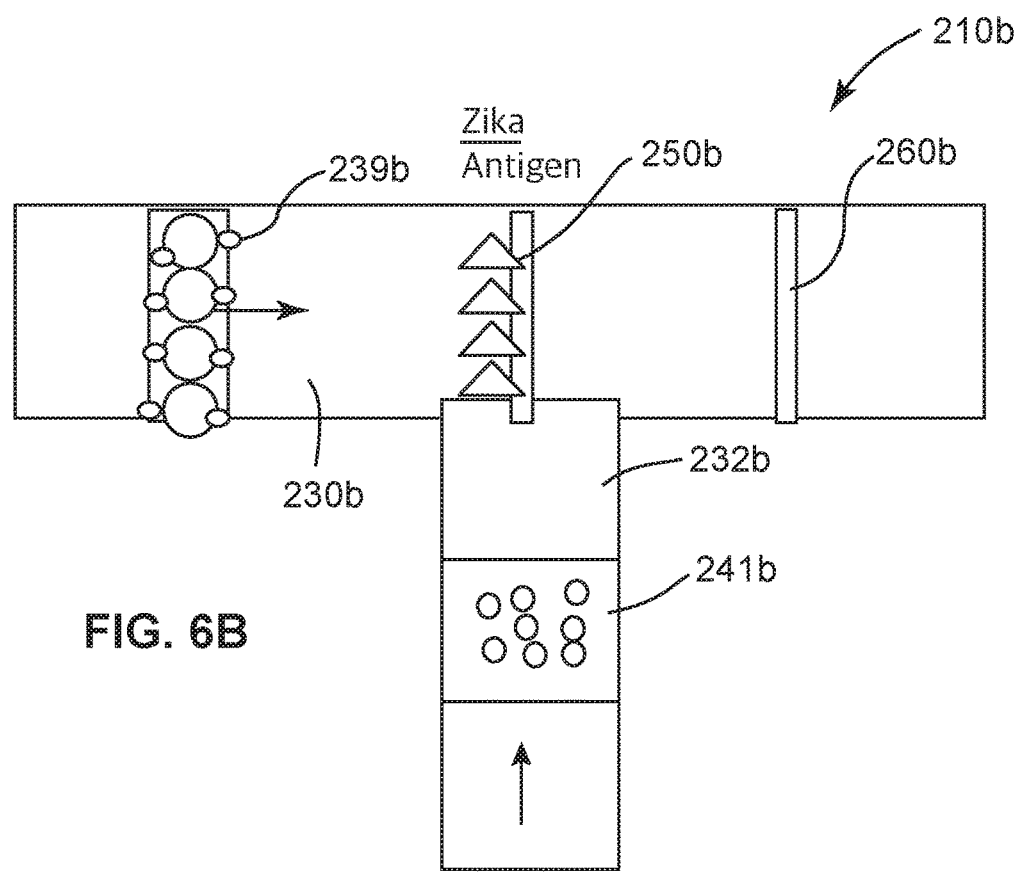

While FIGS. 5A-5D are directed to immunoassays for Dengue IgG and Dengue IgM, it will be appreciated that a highly specific immunoassay for any flavivirus or alphavirus may be generated using the teachings herein, and by adjusting the specifics of the test line and the depletion zone. By way of example only, highly specific immunoassays for Zika IgG are seen in FIGS. 6A and 6B. The immunoassay 210a of FIG. 6A is essentially identical to immunoassay 110a of FIG. 5A (e.g., with sorbent strips 230a, 232a, a gold sol conjugated to Protein A or anti-human IgG 239a, test line 250a, and control line 260a), except that the test line 250a has immobilized Zika antigen instead of immobilized Dengue antigen, and the depletion zone is provided with second conjugates 241a of particles (e.g., latex) conjugated to one or more specific antigens against viruses that are different than but related to and cross-reactive with Zika such as antigens of one or more of Dengue, Chikungunya, West Nile, and Yellow fever. Accordingly, the second conjugate is used as a depleting mechanism that captures and thereby depletes antibodies different than but related to the Zika antibodies that are to be detected at the test site.

Similarly, the highly specific immunoassay 210b of FIG. 6B is essentially identical to immunoassay 110c of FIG. 5C (with sorbent strips 230b, 232b, conjugate 239b, test line 250b, and control line 260b) except that test line 250b has immobilized Zika antigen instead of immobilized Dengue antigen, and the depletion zone is provided with one or more recombinant antigens 241b against viruses that are different than but related to and cross-reactive with Zika such as recombinant antigens of one or more of Dengue, Chikungunya, West Nile, and Yellow ever which may be mixed with a stabilizer/blocker and sprayed on the sorbent strip 232b. Accordingly, the recombinant antigens are used as a depleting mechanism that captures and depletes antibodies different than but related to the Zika antibodies that are to be detected at the test site.

The immunoassay apparatuses of FIGS. 6A and 6B are used in the same manner and in function in the same manner as those previously described with respect to FIGS. 5A-5D.

Figure 7A:
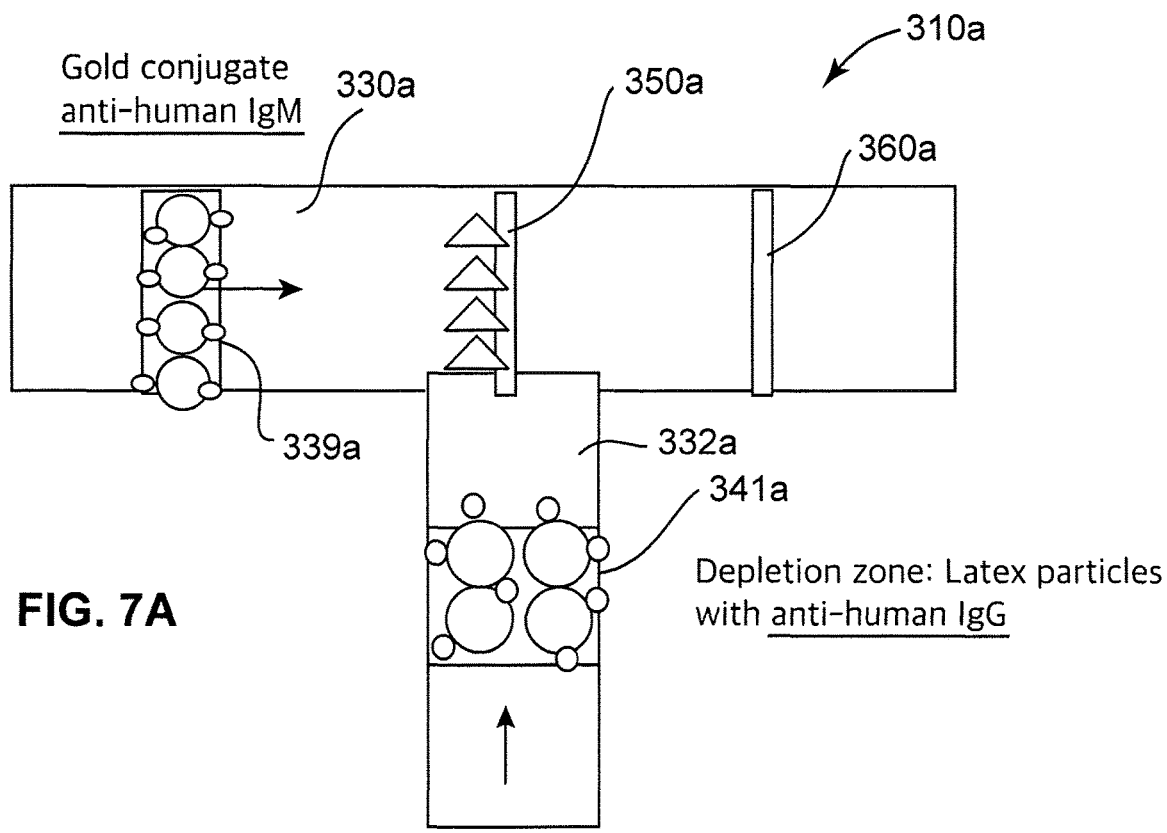

Turning now to FIG. 7A, an immunoassay 310a for detecting a flavivirus IgM or alphavirus IgM is shown. The immunoassay 310a is similar to the immunoassay device of FIG. 5B, except that the depletion zone, rather than being provided with a conjugate of latex and specific recombinant antigens or synthetic peptides is provided with a conjugate 341a of latex particles conjugated with anti-human IgG antigen. Thus, immunoassay 310a includes first and second sorbent materials 330a, 332a, a marker conjugate 339a with anti-human IgM antigen conjugated to particles (e.g., gold sol) and located in or on the flow path of the first sorbent material 330a, the depletion zone with the aforementioned conjugate 341a of latex particles conjugated with anti-human IgG antigen in or on the flow path of the second sorbent material 332a, a test line 350a with the immobilized flavivirus or alphavirus IgM antigen (e.g., Zika IgM antigen or Dengue IgM antigen, or Chikungunya IgM, etc.) at the junction of the first and second sorbent materials, and a control line 360a. The provided immunoassay device 310a is used in the same manner as previously described devices, but functions differently from those devices due to the fact that the conjugate 341a of the depletion zone is not provided with recombinant antigens that are different than but related to the test line antigen. Rather, the depletion zone conjugates 341a are directed to broadly depleting IgG antibodies, including all IgG antibodies of flaviviruses and alphaviruses that may be related to the flavivirus or alphavirus being detected, other IgG antibodies that may not be related to the flavivirus or alphavirus being detected, and even IgG antibodies of the flavivirus or alphavirus being detected. At the same time, IgM antibodies of the flavivirus or alpharvirus being detected, if present in the sample, will not be significantly depleted and will migrate down to the test line 350a where they will bind with the flavivirus or alphavirus IgG antigen. When the marker conjugate 339a on the flow path of the first sorbent material 330a is washed down to the test line 350a containing the IgM antibodies of the flavivirus or alphavirus being detected, the anti-human IgM antigen of the marker conjugate 339a will bind to free binding sites on the IgM antibodies of the sample at the test line 350a, thereby providing a detectable (e.g., visible) result.

According to one aspect, by depleting IgG antibodies, an immunoassay with a high sensitivity to IgM antibodies is obtained, because IgG antibodies that would otherwise bind to the common antigen at the test line and thereby decrease the capacity of IgM binding, will be depleted.

In some embodiments, the depletion conjugates are sprayed onto the sorbent material which will carry the sample. Where latex particles are used in the depletion conjugate, the latex particles may be size selected to provide control of depletion reagents. Depending upon the sorbent material, relatively smaller particles (e.g., under 1000 nm diameter) may be able to migrate if not otherwise immobilized, whereas larger size particles (e.g., over 1000 nm diameter) may be trapped.

Figure 7B:
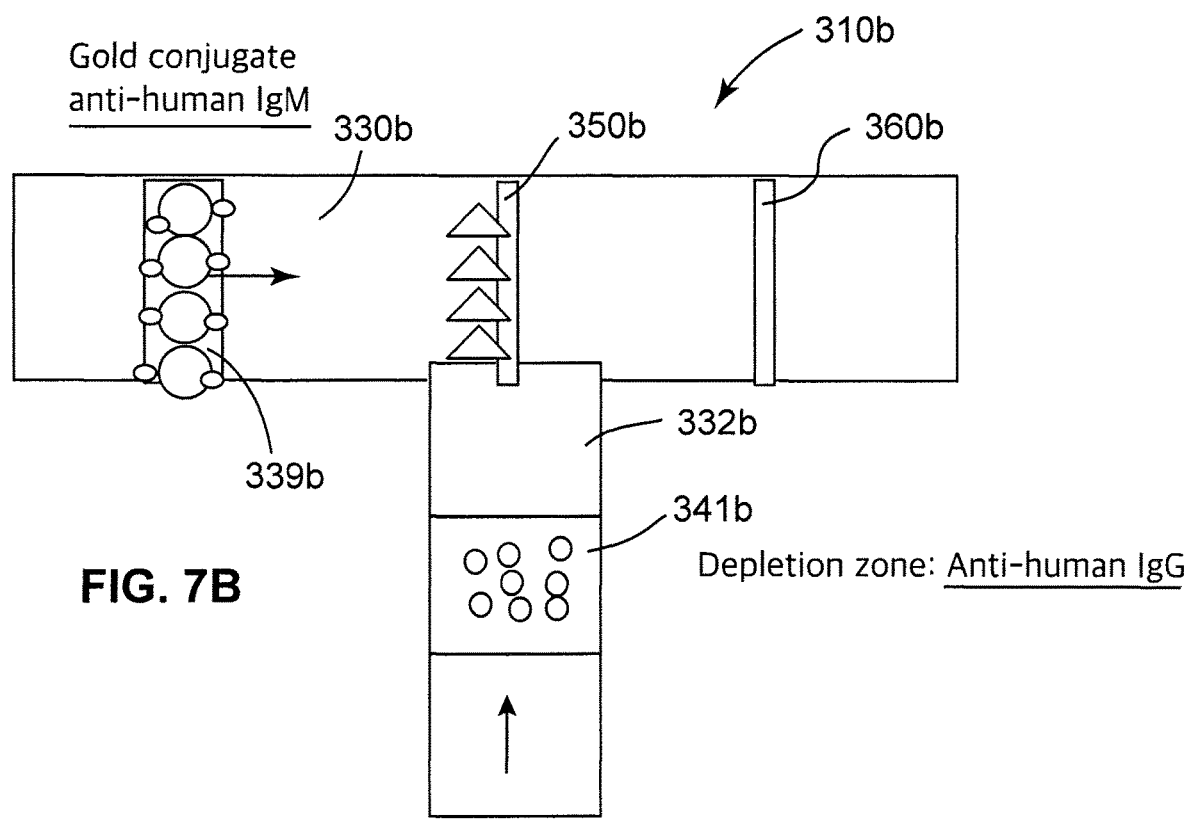

Another immunoassay 310b is shown in FIG. 7b. Immunoassay 310b is similar to immunoassay 310a (with sorbent strips 330b, 332b, anti-human IgM conjugate 339b, test line 350b having the immobilized flavivirus or alphavirus IgM antigen, control line 360b, etc.) except that instead of providing conjugates 341a with latex particles and anti-human IgG, the depletion zone of immunoassay 310b utilizes a mixture 341b of the same anti-human IgG antibodies previously described with respect to immunoassay 310a, but mixed with a stabilizer/blocker and sprayed onto the depletion zone of the sample migration path of sorbent strip 332b. The immunoassay 310b is used in the same manner and will function substantially in the same manner as immunoassay 310a, except that the depletion mixture 341b is more likely to migrate if not otherwise immobilized.

The immunoassay apparatuses of FIGS. 7A and 7B are used in the same manner and in function in the same manner as those previously described with respect to FIGS. 5A-5D.

Figure 8:
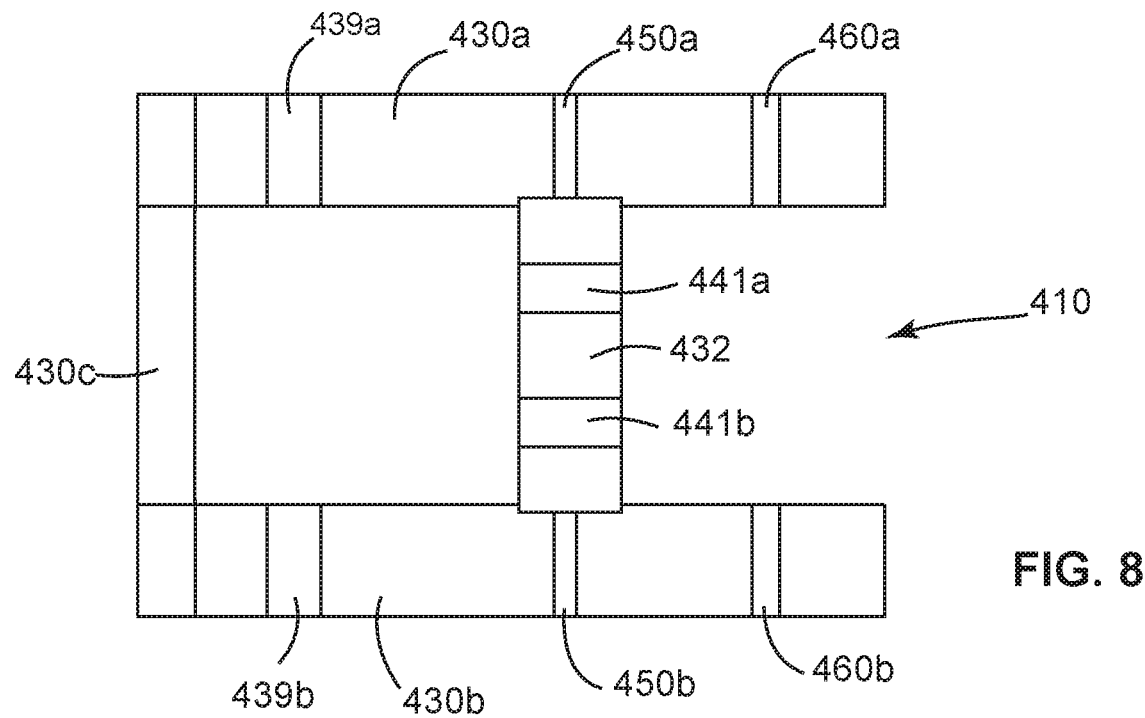
FIG. 8 is a diagram of an IgM/IgG immunoassay device test cell.

Turning now to FIG. 8, another immunoassay 410 is seen. Immunoassay 410 is directed to detecting both a flavivirus (or alphavirus) IgM antibody and a flavivirus (or alphavirus) IgG antibody. The immunoassay 410 includes (i) a first sorbent strip 430a with marker conjugate 439a having anti-human IgM antigen conjugated to particles (e.g., gold sol) located in or on the flow path of the first sorbent material 430a, (ii) a second sorbent strip 432, separate and distinct from the first sorbent strip, for receiving the sample and containing a first depletion zone with either conjugates 441a of latex particles conjugate with anti-human IgG or a mixture of the same anti-human IgG antibodies with a stabilizer/blocker which are sprayed onto the first depletion zone, and a second depletion zone (distinct from the first depletion zone) with either conjugates 441b of latex and specific recombinant antigens or synthetic peptides of flaviviruses (or alphaviruses) or a mixture of the same with a stabilizer/blocker which are sprayed onto the second depletion zone, and (iii) a third sorbent strip 430b (separate and distinct from the second sorbent strip) with marker conjugate 439b of Protein A or anti-human IgG coupled to particles such as gold sol. The immunoassay has at least one first test line 450a having at least one immobilized first flavivirus antigen located at an intersection of the first sorbent strip 430a and second sorbent strip 432, and at least one second test line 450b with at least one immobilized flavivirus antigen located at an intersection of the third sorbent strip 430b and the second sorbent strip 432. First and second control lines 460a, 460b may be located on the first and third sorbent strips. If desired, a fourth sorbent strip 430c may be provided to connect the first and third sorbent strips 430a, 430b. In one embodiment, for convenience, the first, third and fourth sorbent strips are integral with each other such that buffer applied to single location at a portion of the strip (the "fourth" sorbent strip) will spread to both the first and third sorbent strips and push the respective marker conjugates 439a, 439b to the respective test lines 450a, 450b and control lines 460a, 460b. In one embodiment, the second sorbent strip 432 may be split up into two separate strips, with one containing the first depletion zone and the other containing the second depletion zone. For convenience, it may be useful that the second sorbent strip be a single strip so that a single sample applied at a location between the two conjugate zones will migrate (independently or using a buffer) to the respective depletion zones 431a, 431b and then to the respective test lines 450a, 450b.

It will be appreciated that immunoassay 410 has aspects that are similar to both the immunoassay device 110a of FIG. 5A and the immunoassay device 310a of FIG. 7A. More particularly, the first sorbent strip 430a with test zone 450a and the portion of the second sorbent strip 432 containing depletion conjugates or molecules for broadly depleting IgG antibodies function much in the same manner as the immunoassays 310a and 310b of FIGS. 7A and 7B for detecting IgM antibodies. Indeed, depletion zone 441a depletes all IgG antibodies, including flaviviruses and alphaviruses that may be related to the flavivirus or alphavirus being detected, other IgG antibodies that may not be related to the flavivirus or alphavirus being detected, and even IgG antibodies of the flavivirus or alphavirus being detected. At the same time, IgM antibodies of the flavivirus or alpharvirus being detected, if present in the sample, will not be significantly depleted and will migrate down to the test line 450a where they will bind with the flavivirus or alphavirus IgG antigen. When the marker conjugate 439a on the flow path of the first sorbent material 430a is washed down (by buffer) to the test line 450a containing the IgM antibodies of the flavivirus or alphavirus being detected, the anti-human IgM antigen of the marker conjugate 439a will bind to free binding sites on the IgM antibodies of the sample at the test line 450a, thereby providing a detectable (e.g., visible) result much as described in the immunoassays 310a and 310b of FIGS. 7A and 7B. At the same time, the third sorbent strip 430c with test zone 450b and the portion of the second sorbent strip 432 containing molecules for depleting cross-reactive antibodies to the antibody being tested for at test line 450b function much in the same manner as the immunoassays 110a and 110c of FIGS. 5A and 5C. Indeed depletion zone 441b is provided with specific recombinant antigens or synthetic peptides of flaviviruses (or alphaviruses) for depleting antibodies of flaviviruses (and alphaviruses) related to but different than the flavivirus (or alphavirus) being tested at the test zone. Thus, when the marker conjugate 439b on the flow path of the third sorbent material 430c is washed down (by buffer) to the test line 450b containing the IgG antibodies of the flavivirus or alphavirus being detected, the Protein A or anti-human IgG of the marker conjugate 439b will bind to free binding sites on the IgG antibodies of the sample at the test line 450b, thereby providing a detectable (e.g., visible) result much as described in the immunoassays 210a and 210c of FIGS. 5A and 5C.

The immunoassay of FIG. 8 may be utilized as follows. First, a sample (not shown) possibly containing IgG and/or IgM antibodies for the disease(s) being tested for is optionally diluted (e.g., with buffer) and provided to the second sorbent strip between the depletion zones. The sample does not immediately wet the test sites but is allowed to take time to migrate from its location of application to the depletion zones, and then to the test sites. If the sample is not first diluted, optionally, after providing the sample to the second sorbent strip, a measured amount of liquid such as a buffer solution may be added to the second sorbent strip to help in the migration of the sample. Regardless, if the sample includes antigens or antibodies that react with the antigens in one or both of the depletion zones, those antibodies are captured at the depletion zones and are depleted from the sample before reaching the respective test lines. To the extent that the antigens of the depletion zones are not immobilized, or loosen from the sorbent strip and travel down to the test sites, many of the reactive sites on the antibodies of the related flaviviruses and/or alphaviruses are occupied with depletion zone recombinant antigens so that they will not bind to the antigen at the test line. Conversely, to the extent that antibodies of interest are present in the sample, they will generally not be depleted significantly by the specific antigens in the depletion zone, but will travel down to the test line and bind to the antigens immobilized at the test lines. A sufficient time after application of the sample to the second sorbent strip of the immunoassay, a liquid such as a buffer solution is added to the first and third sorbent strips (e.g., via the fourth sorbent strip). The solution is added to a location which permits it to cause the conjugates on the first and third sorbent strips to migrate to the respective test sites (and control sites, if provided), and to bind with the antibodies of the sample (if present) that are captured at the respective test sites. The test sites and control sites are then inspected in order to determine whether the sample is "positive" or not. Typically, a "positive" test indicating the presence of the antibody in the sample is obtained when both the test site and the control site show lines of color. A "negative" test indicating the lack of the presence of the antibody in the sample is obtained when only the control site shows a line of color.

The use of the immunoassay apparatus may be expedited by providing a housing for the sorbent strips, with the housing having holes and numbering and/or lettering to indicate that one hole in the housing is for receiving the sample (and optionally some buffer) and is to be used first, and that another hole (or holes) is for receiving the buffer solution that moves the marker conjugate and is to be used second.

According to one aspect, the immunoassay 410 may be directed to detecting IgG and IgM antibodies of a single flavivirus or alphavirus disease (e.g., Dengue, Zika, Chikungunya, etc.), or IgG antibodies to one disease and IgM antibodies to another disease. Thus, in one aspect, in some circumstances it may be useful to know whether an individual was previously infected by a first disease (such as Dengue—as shown by the IgG test line) and is currently being infected by a new infection of the same disease (as shown by the IgM test line). In other aspect, in some circumstances it may be useful to know whether an individual is currently being infected by one disease (such as Zika) but was previously infected another disease (such as Dengue).

Figure 9:
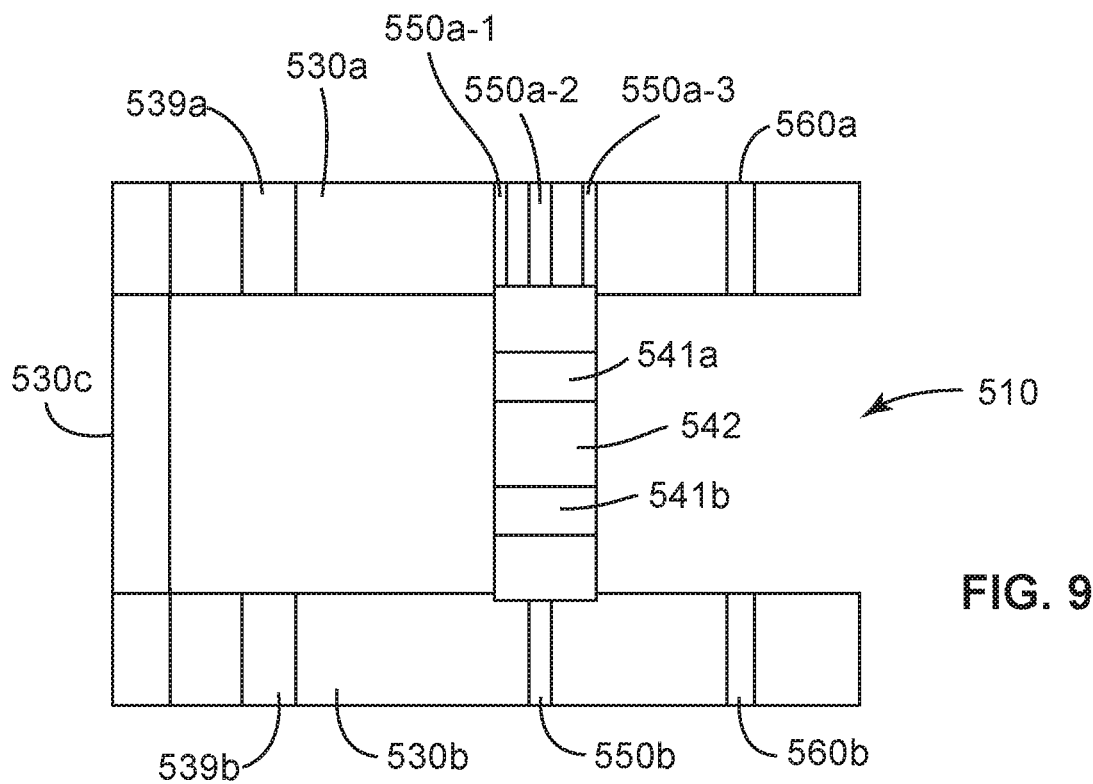
FIG. 9 is a diagram of another IgM/IgG immunoassay device test cell.

In FIG. 9, another immunoassay 510 is seen. Immunoassay 510 is directed to detecting both flavivirus (or alphavirus) IgM antibodies of multiple diseases and flavivirus (or alphavirus) IgG antibodies of one or more diseases. The immunoassay 510 includes (i) a first sorbent strip 530a with marker conjugate 539a having anti-human IgM antigen conjugated to particles (e.g., gold sol) located in or on the flow path of the first sorbent material 530a, (ii) a second sorbent strip 532, separate and distinct from the first sorbent strip, for receiving the sample and containing a first depletion zone with either conjugates 541a of latex particles conjugate with anti-human IgG or a mixture of the same anti-human IgG antibodies with a stabilizer/blocker which are sprayed onto the first depletion zone, and a second depletion zone (distinct from the first depletion zone) with either conjugates 541b of latex and specific recombinant antigens or synthetic peptides of flaviviruses (or alphaviruses) or a mixture of the same with a stabilizer/blocker which are sprayed onto the second depletion zone, and (iii) a third sorbent strip 530b (separate and distinct from the second sorbent strip) with marker conjugate 539b of Protein A or anti-human IgG coupled to particles such as gold sol. Immunoassay 510 has first test lines 550a-1, 550a-2, 550a-3 having immobilized flavivirus antigens located at an intersection of the first sorbent strip 530a and second sorbent strip 532, and at least one second test line 550b with at least one immobilized flavivirus antigen located at an intersection of the third sorbent strip 430b and the second sorbent strip 432. First and second control lines 560a, 560b may be located on the first and third sorbent strips. If desired, a fourth sorbent strip 530c may be provided to connect the first and third sorbent strips 530a, 530b. In one embodiment, for convenience, the first, third and fourth sorbent strips are integral with each other such that buffer applied to single location at a portion of the strip (the "fourth" sorbent strip) will spread to both the first and third sorbent strips and push the marker conjugate 539a to the test lines 550a-1, 550a-2, 550a-3 (and control line 560a) and marker conjugate 539b to test line 550b and control line 460b. In one embodiment, the second sorbent strip 532 may be split up into two separate strips, with one containing the first depletion zone and the other containing the second depletion zone. For convenience, it may be useful that the second sorbent strip be a single strip so that a single sample applied at a location between the two conjugate zones will migrate (independently or using a buffer) to the respective depletion zones 531a, 531b and then to the respective test lines.

It will be appreciated that immunoassay 510 is similar to immunoassay 410 except that it is capable of testing for current infection by multiple diseases and is capable of testing for at least one previous infection. More particularly, the first sorbent strip 530a with test zones 550a-1, 550a-2, 550a-3 and the portion of the second sorbent strip 532 containing depletion conjugates or molecules for broadly depleting IgG antibodies function much in the same manner as the immunoassay 410 of FIG. 8 for detecting IgM antibodies, except that IgM antibodies of multiple diseases are being detected. Indeed, depletion zone 541a depletes IgG antibodies, including IgG antibodies of flaviviruses and alphaviruses that may be related to the flavivirus(es) and/or alphavirus(es) being detected, other IgG antibodies that may not be related to the flaviviruses and/or alphaviruses being detected, and even IgG antibodies of the flaviviruses and/or alphaviruses being detected. At the same time, IgM antibodies of the flaviviruses and/or alpharviruses being detected, if present in the sample, will not be significantly depleted and will migrate down to the test line 550a-1, 550a-2, 550a-3 where they will bind with the flavivirus and/or alphavirus IgG antigens. When the marker conjugate 539a on the flow path of the first sorbent material 530a is washed down (by buffer) to the test lines 550a-1, 550a-2, 550a-3 containing the IgM antibodies of the flaviviruses and/or alphaviruses being detected, the anti-human IgM antigen of the marker conjugate 539a will bind to free binding sites on the IgM antibodies of the sample, if present at the one or more test lines, thereby providing detectable (e.g., visible) results; both positive and negative. It should be noted, however, that because of cross-reactivity between the flaviviruses and/or alphaviruses, it is possible that even where there are no antibodies for a particular flavivirus or alphavirus being tested, the test line may show a weak positive result. However, by comparing the results of that test line to a true positive test line, it will be determined that the weak positive result is not a true positive test result, but just the result of cross-reactivity. By way of example, line 550a-1 may comprise Zika-specific antigen, line 550a-2 may comprise Dengue-specific antigen, and line 551a-3 comprise may Chikungunya-specific antigen. Assuming the sample contains Dengue IgM antibodies and no Chikungunya or Zika IgM antibodies, it is expected that line 550a-2 will show a positive result and that lines 550a-1 and 550a-3 will show no color. However, even if some marker-conjugate attaches at lines 550a-1 and 550a-3 due to cross-reactivity, the relative strengths of the signals at those lines will be small relative to the strength of the signal of line 550a-2, thus signifying a negative result. It will also be appreciated that if the sample, for example, contained both Dengue and Zika IgM antibodies, the signals at lines 550a-1 and 550a-2 will show a positive result, and any signal at line 550a-3 will be small relative to the signals at lines 550a-1 and 550a-2.

At the same time, the third sorbent strip 530c with the one or more test zones 550b and the portion of the second sorbent strip 532 containing molecules for depleting cross-reactive antibodies to the antibody being tested for at test line(s) 550b function much in the same manner as the immunoassays 110a and 110c of FIGS. 5A and 5C. Indeed depletion zone 541b is provided with specific recombinant antigens or synthetic peptides of flaviviruses (or alphaviruses) for depleting antibodies of flaviviruses (and alphaviruses) related to but different than the flavivirus (or alphavirus) being tested at the test zone. Thus, when the marker conjugate 539b on the flow path of the third sorbent material 530c is washed down (by buffer) to the test line 550b containing the IgG antibodies of the flavivirus or alphavirus being detected, the Protein A or anti-human IgG of the marker conjugate 539b will bind to free binding sites on the IgG antibodies of the sample at the test line 550b, thereby providing a detectable (e.g., visible) result much as described in the immunoassays 510a and 510c of FIGS. 5A and 5C.

In one embodiment, more than one test line is provided at the intersection of the second sorbent strip 532 and the third sorbent strip 530b for detecting IgG antibodies of more than one disease. In such a case, the depletion molecules 541b may include depletion molecules for diseases different than but related to the diseases for which the test is being provided. For example, if test lines are provided for detecting IgG antibodies to Zika and Dengue, the depletion molecules 541b may include depletion molecules for, e.g., Chikungunya, West Nile virus, and Yellow fever. Again, while there may be cross-reactivity, the relative strength of the test lines may provide an indication as to whether the antibodies are present, or whether cross-reactivity is being detected.

In another embodiment, the depletion molecules 541b may not include depletion molecules for the diseases different than but related to the diseases for which the test is being provided, but may include recombinant antigens or synthetic peptides against cross-reactive portions (e.g., the envelope (EP)) of the antibodies for the diseases for which the test is being provided, and the test lines may include non-structural antigen (e.g., NS1) for detection of the specific IgG of the same antibodies. The envelope (EP) antigen has higher cross-reactivity between Dengue and Zika virus and therefore a depletion reagents could be designed with EP antigen to remove cross-reacting antibodies to the Zika virus. The Non-Structural antigen (NS1) is more specific for Dengue and Zika and therefore it could be use as capture line in the membrane for achieving higher specificity. It is also possible to use specific domain (Zika-EDI) Zika virus as depletion and another specific domain (Zika-EDIII) Zika virus as a capture.

The immunoassay of FIG. 9 may be utilized as follows. First, a sample (not shown) possibly containing IgG and/or IgM antibodies for the diseases being tested for is optionally diluted (e.g., with buffer) and provided to the second sorbent strip between the depletion zones. The sample does not immediately wet the test sites but is allowed to take time to migrate from its location of application to the depletion zones, and then to the test sites. If the sample is not first diluted, optionally, after providing the sample to the second sorbent strip, a measured amount of liquid such as a buffer solution may be added to the second sorbent strip to help in the migration of the sample. Regardless, if the sample includes antigens or antibodies that react with the antigens in one or both of the depletion zones, those antibodies are captured at the depletion zones and are depleted from the sample before reaching the respective test lines. To the extent that the antigens of the depletion zones are not immobilized, or loosen from the sorbent strip and travel down to the test sites, many of the reactive sites on the antibodies of the related flaviviruses and/or alphaviruses are occupied with depletion zone recombinant antigens so that they will not bind to the antigen at the test line. Conversely, to the extent that antibodies of interest are present in the sample, they will generally not be depleted significantly by the specific antigens in the depletion zone, but will travel down to the test line and bind to the antigens immobilized at the test lines. A sufficient time after application of the sample to the second sorbent strip of the immunoassay, a liquid such as a buffer solution is added to the first and third sorbent strips (e.g., via the fourth sorbent strip). The solution is added to a location which permits it to cause the conjugates on the first and third sorbent strips to migrate to the respective test sites (and control sites, if provided), and to bind with the antibodies of the sample (if present) that are captured at the respective test sites. The test sites and control sites are then inspected in order to determine whether the sample is "positive" or not. Typically, a "positive" test indicating the presence of the antibody in the sample is obtained when both the test site and the control site show lines of color. A "negative" test indicating the lack of the presence of the antibody in the sample is obtained when only the control site shows a line of color. As with the previously described embodiments, the use of the immunoassay apparatus may be expedited by providing a housing for the sorbent strips, with the housing having holes and numbering and/or lettering to indicate that one hole in the housing is for receiving the sample (and optionally some buffer) and is to be used first, and that another hole (or holes) is for receiving the buffer solution that moves the marker conjugate and is to be used second.

There have been described and illustrated herein several embodiments of immunoassays and methods of their use. While particular embodiments have been described, it is not intended that the claims be limited thereto, as it is intended that the claims be as broad in scope as the art will allow and that the specification be read likewise. Thus, while the specification discusses ligand binding using antigen/antibody reactions, other ligand binding mechanisms such as aptamer binding, nucleic acid binding, enzymatic binding, etc. may also be used. Also, while the test cells are described as having a single line for testing for a single ligand, it will be appreciated that two or more lines may be utilized for testing for more than one ligand. Further, while the test cells are described as having holes in the top wall of a housing for receiving the sample and the buffer-solution or buffer-conjugate subsystem, it will be appreciated that one or both holes may be provided in the end wall or side wall of the housing. Similarly, while the sorbent material was described as preferably including a thin plastic backing, it will be appreciated that the plastic backing could be provided only at certain locations or not be provided at all. Where only partial backings or no backings are provided, the test and control sites can be located on either or both sides of the sorbent material. Further yet, while a test strip and control strip are shown is being rectangular in configuration (i.e., lines), it will be appreciated that the test and control sites can be configured differently such as in circles, squares, ovals, a broken line, etc. In fact, the test site and control site can be configured differently from each other.

Those skilled in the art will also appreciate that the housing may be modified in additional ways to include separate windows for each test line. Also, while the embodiments were described in conjunction with the use of a buffer solution which is added to the migration path of the conjugate and optionally to the migration path of the sample, it will be appreciated that that one or more buffers may be chosen as desired to be added to the migration paths depending upon the test or tests to be conducted. Thus, buffers such as phosphate buffers or TRIS (tris hydroxymethylaminomethane) buffers are often utilized. However, the embodiments are intended to encompass the use of any diluent including water. In addition, the diluent may, if needed, may be added to and mixed with the sample prior to adding the sample to the sorbent material or the sample may be deposited first and the diluent may be added thereafter. Likewise, any diluent capable of causing the conjugate of the "non-sample" path to migrate may be utilized, and may be premixed with the conjugate in a liquid conjugate system, or provided to the migration path for the conjugate in a dry conjugate system.

Those skilled in the art will also appreciate that while the embodiments were described with particular reference to detection of a flu antibody, particular flaviviruses and alphaviruses, and HIV p-24 antigen, the apparatus and methods may be useful in detection of other antibodies or antigens whether human or animal. Also, while the embodiments were described with particular reference to the use of blood as a sample, it will be appreciated that other body fluids or excretions, or blood portions may be utilized including, but not limited to urine, feces, saliva, spitum, blood serum (plasma), etc. It will therefore be appreciated by those skilled in the art that yet other modifications could be made without deviating from the spirit and scope of the claims.

What is claimed is:

1. A test device for determining the presence of a first ligand in a liquid sample, comprising:
   a) a first sorbent strip having a first location for receiving a solution and defining a first migration path;
   b) a marker conjugate adapted to move along said first migration path and bind to said first ligand;
   c) a second sorbent strip distinct from said first sorbent strip and having a second location for receiving the liquid sample and defining a second migration path;
   d) depletion molecules located on or in said second migration path wherein said depletion molecules include a ligand-binding elements adapted to specifically bind to second ligands that are different from but related to said first ligand by being cross-reactive therewith, and to which said depletion molecules will not substantially bind, and wherein said depletion molecules located on or in said second migration path are sprayed on said second migration path and are not immobilized;
   e) a test site located on or in one at least one of said first sorbent strip and said second sorbent strip, said test site having an immobilized first ligand binding mechanism for said first ligand, and said first and second sorbent strips touching each other at the test site location, wherein said second location is removed from said test site such that sample applied to said second location requires time to migrate to said test site and does not immediately wet said test site.

2. A test device according to claim 1, wherein: said first ligand is a first flavivirus antibody, said second ligands that are different from but related to said first ligand include at least one of a second flavivirus antibody and an alphavirus antibody, and said ligand-binding elements are antigens specific to at least one of a second flavivirus antibody and an alphavirus antibody.

3. A test device according to claim 2, wherein: said first flavivirus antibody is a Dengue antibody, and said antigens specific to at least one of a said second flavivirus antibody and an alphavirus antibody are antigens specific to Zika antibodies.

4. A test device according to claim 2, wherein: said antigens specific to at least one of a said second flavivirus antibody and an alphavirus antibody are antigens specific to at least one of West Nile and Yellow fever antibodies.

5. A test device according to claim 2, wherein: said first flavivirus antibody is a Zika antibody, and said antigens specific to at least one of a said second flavivirus antibody and an alphavirus antibody are antigens specific to Dengue antibodies.

6. A test device according to claim 5, wherein: said antigens specific to at least one of a said second flavivirus antibody and an alphavirus antibody are antigens specific to at least one of West Nile and Yellow fever antibodies.

7. A test device according to 1, wherein: said first ligand is a first flavivirus antibody, said second ligands that are different from but related to said first ligand include at least one alphavirus antibody, and said ligand-binding elements are antigens specific to at least one of a second flavivirus antibody and an alphavirus antibody include antigens specific to an alphavirus antibody.

8. A test device according to claim 7, wherein: said first flavivirus antibody is one of a Dengue antibody and a Zika antibody, and said antigens specific to an alphavirus antibody are specific to a Chikungunya antibody.

9. A test device according to claim 8, wherein said antigens specific to at least one of a said second flavivirus antibody and an alphavirus antibody are antigens specific to at least one of West Nile and Yellow fever antibodies.

10. A test device according to claim 1, wherein said depletion molecules comprise conjugates of latex particles with antigens specific to at least one of a second flavivirus antibody and an alphavirus antibody.

11. A test device according to claim 1, wherein said depletion molecules comprise conjugates of latex particles and either (i) recombinant antigens, (ii) synthetic peptides, or (iii) lysate antigens, specific to at least one of a second flavivirus antibody and an alphavirus antibody.

12. A test device according to claim 1, further comprising: a housing defining a first opening adjacent said first location, a second opening adjacent said second location, and a window adjacent said test site through which said test site is viewable.

13. A test device according to claim 1, wherein: said marker conjugate comprises an antigen or antibody for the first ligand and a marker coupled to the antigen or antibody.

14. A test device according to claim 13, wherein: said marker is a colored marker viewable in the visible spectrum.

15. A test device according to claim 14, wherein: said first sorbent strip and said second sorbent strip are arranged in a "T" configuration.

16. A test device according to claim 12, wherein: at least one of said first sorbent strip and said second sorbent strip includes a control site, and either said window is sized to permit viewing of said control site or a second window is provided in said housing to permit viewing of said control site.

17. A test device according to claim 1, further comprising: buffer solution, wherein said marker conjugate is disposed on or in said first migration path and said buffer solution is adapted to carry said marker conjugate to said test site.

18. A test device according to claim 12, further comprising: a first adhesive backing card underlying or overlying said first sorbent strip, and a second adhesive backing card underlying or overlying said second sorbent strip, wherein said first sorbent strip includes a first membrane and a first backing and said second sorbent strip includes a second membrane and a second backing, and said first sorbent strip and said second sorbent strip are arranged such that said first membrane is in contact with said second membrane.

19. A test device according to claim 2, wherein said first ligand is a first flavivirus IgM antibody, said second ligands that are different from but related to said first ligand include at least one of a second flavivirus antibody and an alphavirus antibody, and said ligand-binding elements are antigens specific to at least one of a second flavivirus antibody and an alphavirus antibody.

20. A test device according to claim 1, wherein said first ligand is an IgM ligand and said test device is also for determining the presence of a second ligand in the liquid sample, said second ligand being an IgG ligand, said test device further comprising: a third sorbent strip that receives the solution and defines a third migration path, said third sorbent strip being distinct from said second sorbent strip; a second marker conjugate adapted to move along said third migration path and bind to said second ligand; a fourth sorbent strip defining a fourth migration path; second depletion molecules located on or in said fourth migration path; and a second test site located on or in one at least one of said third sorbent strip and said fourth sorbent strip, said second test site having an immobilized second ligand binding mechanism for said second ligand, and said third and fourth sorbent strips touching each other at the second test site location.

21. A test device according to claim 20, wherein said second and fourth sorbent strips are integral with each other.

22. A test device according to claim 20, wherein said first and third sorbent strips are connected to and in fluid contact with each other by other than said second and fourth sorbent strips.

23. A test device according to claim 20, wherein said second conjugate marker includes anti-human IgG, and said second depletion molecules include anti-human IgM.

24. A test device according to claim 23, wherein said test device is also for determining the presence of a plurality of different second ligands in the liquid sample, and said second test site having an immobilized second ligand binding mechanism for said second ligand comprises a plurality of test lines having a plurality of different immobilized second ligand binding mechanisms for said plurality of different second ligands.

25. A test device according to claim 23, wherein said first ligand is an IgM ligand of a first flavivirus and said second ligand is an IgG ligand of said first flavivirus.

26. A test device according to claim 23, wherein said first ligand is an IgM ligand of a first flavivirus and said second ligand is an IgG ligand of a second flavivirus or alphavirus different than said first flavivirus.

27. A method for testing a sample for the presence of a first flavivirus ligand, comprising:
   a) obtaining a test device having a first sorbent strip having a first location for receiving a solution and defining a first migration path, a marker conjugate located on or in said first migration path, said marker conjugate adapted to bind to said first ligand, a second sorbent strip distinct from said first sorbent strip and having a second location for receiving the liquid sample and defining a second migration path, depletion molecules located on or in said second migration path wherein said depletion molecules include a ligand-binding element including antigens specific to at least one of a second flavivirus antibody and an alphavirus antibody that are adapted to specifically bind to second ligands that are different from but related to said first flavivirus ligand to which said depletion molecules will not substantially bind wherein said depletion molecules are sprayed on said second migration path and are not immobilized, and a test site located on or in at least one of said first sorbent strip and said second sorbent strip, said test site having an immobilized ligand-binding mechanism for said first flavivirus ligand, and said first and second sorbent strips touching each other at the test site location, wherein said second location is removed from said test site such that sample applied to said second location requires time to migrate to said test site and does not immediately wet said test site;
   b) applying the sample to said second location;
   c) after said applying the sample, applying a solution to the first location to cause said marker conjugate to migrate along said first migration path; and
   d) inspecting said test site to determine an indication of the presence or lack thereof of the first flavivirus ligand in the sample.

* * * * *